US006399078B1

(12) United States Patent
Devico et al.

(10) Patent No.: US 6,399,078 B1
(45) Date of Patent: Jun. 4, 2002

(54) CHEMOKINE—GLYCOSAMINOGLYCAN COMPLEXES AND THEIR USE IN TREATING OR PREVENTING RECEPTOR MEDIATED DISEASES

(75) Inventors: Anthony L. Devico, Alexandria, VA (US); George K. Lewis; Jennifer M. Burns, both of Baltimore, MD (US); Robert Gallo, Bethesda, MD (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 0 days.

(21) Appl. No.: 09/323,719

(22) Filed: Jun. 1, 1999

Related U.S. Application Data

(60) Provisional application No. 60/087,436, filed on Jun. 1, 1998.

(51) Int. Cl.[7] .......................... A61K 47/00; A61K 39/00; A61K 45/00; A61K 38/00; A61K 31/727
(52) U.S. Cl. ................................ 424/278.1; 424/185.1; 424/279.1; 514/2; 514/56; 514/59; 514/885
(58) Field of Search .............................. 514/2, 56, 59, 514/885; 424/278.1, 185.1, 279.1

(56) References Cited

U.S. PATENT DOCUMENTS

| | | |
|---|---|---|
| 5,288,704 A | 2/1994 | Ungheri et al. |
| 5,464,815 A | 11/1995 | Chamow et al. |
| 5,616,688 A | 4/1997 | Cerami et al. |
| 5,717,074 A | 2/1998 | Wolpe et al. |
| 5,795,860 A * | 8/1998 | Witt et al. .................... 514/12 |

FOREIGN PATENT DOCUMENTS

| | | |
|---|---|---|
| EP | 0 310 136 B1 | 10/1988 |
| EP | 0 356 935 B1 | 8/1989 |
| EP | 0 394 409 B1 | 9/1989 |
| WO | WO 90/03791 | 9/1989 |
| WO | WO 97/19696 | 11/1996 |
| WO | WO 97/25350 | 1/1997 |
| WO | WO 97/37005 | 4/1997 |
| WO | WO 97/44055 | 5/1997 |
| WO | WO 97/45543 | 5/1997 |
| WO | WO 97/47318 | 6/1997 |
| WO | WO 97/47319 | 6/1997 |
| WO | WO 97/49373 | 6/1997 |
| WO | WO 98/09642 | 9/1997 |

OTHER PUBLICATIONS

Trikola et al., J. Virol., 1998, vol. 72, pp. 396–404.*
Tramont et al., Ann. Int. Med. 1990, vol. 112, pp. 241–424.*
Schooley et al., Ann. Int. Med. 1990, vol. 112, pp. 247–253.*
Kahn et al., Ann. Int. Med. 1990, vol. 112, pp. 254–261.*
Flaumenhaft et al., J. Cell Biol. vol. 111, pp. 1651–1659, 1990.*
Arenzana–Seisdedos et al. "HIV blocked by chemokine antagonist" *Nature* 383:400, 1996.

Burns et al. "A new monoclonal antibody, mAb 4A12, identifies a role for the glycosaminoglycan (GAG) binding domain of RANTES in the antiviral effect against HIV–1 and intracellular Ca2 + signaling" *J. Exper. Medic.* 188:1917–27, 1998.

Adams, et al., "Hepatocyte growth factor and macrophage inflammatory protein 1β: Structurally distinct cytokines that induce cytoskeletal changes and subset–preferential migration in T cells" *Proc. Natl. Acad. Sci. USA*, 91:7144–48, Jul. 1994.

Baba, et al., "Sulfated Polysaccharides as Potent Inhibitors of HIV–Induced Syncytium Formation: A New Strategy Towards AIDS Chemotherapy" *J Acquir Immune Defic Syndr.*, 3:493–9, 1990.

Batinić, et al., "The V3 Region of the Envelope Glycoprotein of Human Immundeficiency virus Type 1 Binds Sulfated Polysaccharides and CD4–derived Synthetic Peptides*" *J Biol Chem.*, 267(10):6664–71, 1992.

Bozzini, et al., "Heparin–Binding Domain of Human Fibronectin Binds HIV–1 gp120–160 and Reduces Virus Infectivity" *J Medic Virol.*, 54:44–53, 1998.

Callahan, et al., "D Sulfate Blocks Antibody Binding to the Principal Neutralizing Domain of Human Immunodeficiency Type 1 without Interfering with gp 1 Interactions" *J Virol.*, 65:1543–50, 1991.

Cocchi, et al., "Identification of RANTES, MIP–1α, and MIP–1β as the Major HIV–Suppressive Factors Produced by CD8+ T Cells" *Science*, 270:1811–15, 1995.

Conklyn, et al., "Chemokine–Dependent Upregulation of CD11b on Specific Leukocyte Subpopulations in Human Whole Blood: Effect of Anticoagulant on RANTES and MIP–1β Stimulation" *Cytokine*, 8(10):762–66, 1996.

Coombe, et al., "Low anticoagulant heparin retains anti–HIV type 1 activity in Vitro" *Aids Res Hum Retroviruses*, 11(11):1393–6, 1995.

Gilat, et al., "Regulation of Adhesion of CD4+ T Lymphocytes to Intact or Heparinase–Treated Subendothelial Extracelular Matrix by Diffusible or Anchored RANTES and MIP–1β" *J Immunol.* 153:4899–906, 1994.

Guimond, et al., "Activating and Inhibitory Heparin Sequences for FGF–2 (Basic FGF)" *J Biolog Chem.*, 268:23906–14, 1993.

Harrop, et al., "Heparin and its derivatives bind to HIV–1 recombinant envelope glycoproteins, rather than to recombinant HIV–1 receptor, CD4" *Glycobiology*, 8(2):131–7, 1998.

(List continued on next page.)

*Primary Examiner*—Yvonne Eyler
*Assistant Examiner*—Janet L. Andres
(74) *Attorney, Agent, or Firm*—Marianne Fuierer; Steven J. Hultquist; Yongzhi Yang

(57) ABSTRACT

The present invention provides therapeutic compositions of receptor ligand-containing antagonist complexes and methods of using them to treat diseases, disorders or conditions associated with the function or aberrant function of a cell surface receptor.

24 Claims, 7 Drawing Sheets

OTHER PUBLICATIONS

Koopmann et al., "Identification of a Glycosaminoglycan –binding Site in Chemokine Macrophage Inflammatory Protein–1 α*" *J Biol Chem.*, 272(15):10103–09, 1997.

Kuipers, et al., "Mechanism of Anti–HIV Activity of Negatively Charged Albumins Biomolecular Interaction with the HIV–1 Envelope Protein gp120" *J Acquir Immune Defic Syndr Hum Retrovirol.* 11:419–29, 1996.

Kuschert, et al., "[23] Solid–Phase Binding Assay to Study Interaction of Chemokines Methods Enzymol. with Glycosaminoglycans" *Methods Enzymol.*, 287:369–78, 1997.

Lalani, et al., "The Purified Myzoma Virus Gamma Interferon Receptor Homolog M–T7 Interacts with the Heparin –Binding Domains of Chemokines" *J Virol.*, 71(6):4356–63, 1997.

Lederman, et al., "Dextran Sulfate and Heparin Interact with CD4 Molecules to Inhibit the Binding of Coat Protein (gp120) of HIV[1]" *J Immunol.* 143(4):1149–54, 1989.

Luster, et al., "The IP–10 Chemokine Binds to a Specific Cell Surface Heparan Sulfate Site Shared with Platelet Factor 4 and Inhibits Endothelial Cell Proliferation" *J Exp Med.*, 182:219–31, 1995.

Oravecz, et al., "Regulation of Anti–HIV–1 Activity of RANTES by Heparan Sulfate Proteoglycans[1]" *J Immunol.*, 59:4587–92, 1997.

Ohshiro, et al., "Role of Cell Surface Glycosaminoglycans of Human T Cells in Human Immunodeficiency Virus Type–1 (HIV–1) Infection", *Microbiol Immunol.*, 40:827–35, 1996.

Pal, et al., "Inhibition of HIV–1 Infection by the β–Chemokine MDC" *Science*, 278:695–8, 1997.

Parish, et al., "A Polyanion Binding Site on the CD4 Molecule; Proximity to the HIV–gp120 Binding Region[1]" *J Immunol.* 145(4):1188–95, 1990.

Patel, et al., "Cell–Surface Heparan Sulfate Proteoglycan Mediates HIV–1 Infection of T–Cell Lines" *AIDS Res Hum Retroviruses.* 9(2):167–74, 1993.

Rider, et al., "Anti HIV–1 Activity of Chemically Modified Heparins: Correlation Between Binding to the V3 Loop of gp120 and Inhibition of Cellular HIV–1 Infection in vitro" *Biochemistry.* 33:6974–80, 1994.

Rider, Christopher C., "The potential for heparin and its derivatives in the therapy and prevention of HIV–1 infection" *Glycoconjugate J.*, 14:639–42, 1997.

Roderiquez, et al., "Mediation of Human Immunodeficiency Virus Type 1 Binding by Interaction of Cell Surface Heparan Sulfate Proteoglycans with the V3 Region of Envelope gp120–gp41" *J Virol.*, 69:2233–9, 1995.

Selvan, et al., "Heparan Sulfate in Immune Responses" *Annals NY Acad. Sci.* 797:127–39, 1996.

Stringer, et al., "Specific Binding of the Chemokine Platelet Factor 4 to Heparan Sulfate*", *J Biol Chem.* 272(33):20508–14, 1997.

Su, et al., "Heparan Mediates Binding of S–Protein/Vitronectin to the Envelope Glycoprotein of the Human Immunodeficiency Virus and CD4", *Int Arch Allergy Immunol.*, 105:238–44, 1994.

Swart, et al., "The in Vitro Anti–HIV Efficacy of Negatively Charged Human Serum Albumin Is Antagonized by Heparan" *AIDS Res. Human Retrov.*, 13(8):677–83, 1997.

Tanaka, et al., "T–Cell adhesion induced by proteoplycan –immobilized cytokine MIP–1β", *Nature*, 361:79–82, 1993.

Tanaka, et al., "T–Cell Chemotactic Activity of Cytokine LD78: A Comparative Study with Interleukin–8, a Chemotactic Factor for the T–Cell CD45RA+ Phenotype", *Int Arch Allergy Immunol.*, 100:201–8, 1993.

Taylor, et al., "Potent inhibition of human immunodeficiency virus by MDL 101028, a novel sulphonic acid polymer" *Antiv. Res.*, 28:159–173, 1995.

Wagner, et al., "β–Chemokines are released from HIV–1–specific cytolytic T–cell granules complexed to proteoglycans" *Nature*, 391:908–11, Feb. 1998.

Witt, et al., "Differential binding of chemokines to glycosaminoglycan subpopulations" *Curr. Biol.* 4(5):394–400, 1994.

* cited by examiner

CHEMOKINE— GLYCOSAMINOGLYCAN COMPLEXES AND THEIR USE IN TREATING OR PREVENTING RECEPTOR MEDIATED DISEASES

RELATED APPLICATIONS

This application claims priority to the provisional application U.S. Ser. No. 60/087,436, filed Jun. 1, 1998.

1. BACKGROUND OF THE INVENTION

Cell surface receptors play an important role in biology by relaying extracellular messages into intracellular signaling pathways, thereby allowing individual cells to appropriately respond to their surroundings. Such receptors play critical roles in processes including growth control, developmental patterning, hormonal signaling and the immune response. The function of such receptors is thus frequently involved in diseases and conditions involving these processes such as cancer, developmental defects, endocrine disorders, tissue rejection, and autoimmune dysfunctions. These same receptors are also frequently involved in the infection of a host by a pathogenic organism. In particular, many viruses utilize such receptors to facilitate entry into a host cell. These diseases, conditions, and infections are thus amenable to treatment by compounds which are capable of blocking a receptor's function as a mediator of signal transduction or pathogenic intrusion.

Ultimately, there are widespread medical applications for such receptor blocking functions owing to this correspondingly widespread involvement of receptors in organismal function. For example, the recruitment of leukocytes from the circulation to sites of injury and infection is a key process in the physiological response to wound healing and the clearance of pathogenic organisms (Springer (1994) Cell 76: 301–14). Recent advances in the understanding of the molecular mechanisms that regulate leukocyte recruitment have identified a complex interplay between leukocyte, cytokines, chemokines, adhesion molecules, and extracellular matrix components that is essential for directed leukocyte migration. Chemokines comprise an ever enlarging family of small molecular weight cytokines that play a key role as effector molecules which stimulate leukocytes to leave the circulation and migrate to the sites of inflammation and injury. This superfamily of cytokines has well over thirty distinct member, which bind to subsets of G-protein coupled serpentine receptors. Despite the beneficial properties that chemokines have in the wound healing process and for the clearance of infectious organisms, they also can have pathophysiological consequences. Continued expression of chemokines stimulates the accumulation of leukocytes which, when appropriately activated, release injurious enzymes and oxidative radicals. Many inflammatory and immunological disorders, such as arthritis, asthma, reperfusion injury, and atherosclerosis, are characterized by increased levels of specific sets of chemokines. Therefore, a likely target for suppression of inflammatory or immunological disorders is to inhibit chemokine expression or function, thereby limiting the degree of leukocyte infiltration.

Complement activation also plays a fundamental role in inflammation. Inappropriate or excessive activation of the complement system can lead to harmful, potentially life-threatening consequences due to severe inflammatory tissue destruction. These consequences are clinically manifested in various disorders, including septic shock, multiple organ failure and hyperacute graft rejection. In addition, inappropriate activation of the inflammatory response is associated with immune complex and/or autoimmune diseases such as glomerulonephritis and systemic lupus erythematosus (SLE). Such diseases may be triggered by deficiencies in the ability to solubilize and clear circulating immune complexes, leading to the accumulation and deposition of such complexes in blood vessel walls and tissues where they activate the complement cascade and produce local inflammation. Furthermore, such undesirable inflammatory reactions may subsequently augment the antigen presenting functions of mononuclear phagocytes, leading to the abnormal presentation of self antigens—a condition known as autoimmunity. Thus strategies to antagonize components of the complement system would potentially have far ranging applications in the treatment of inflammatory and autoimmune dysfunctions. Indeed, genetic complement deficiencies or complement depletion have been proven to be beneficial in reducing tissue injury in a number of animal models of severe complement- dependent inflammation (Kirschfink M (1997) Immunopharmacology (Netherlands) 38: 51–62).

The complement system relies upon the function of a number of cell surface receptors. These include complement receptor 1 (CR1, also known as C3b Receptor and CD35), complement receptor type 2 (CR2, also known as C3d Receptor and CD21), and complement receptor type 3 (CR3, also known as CR3. MAC-1 and CD11bCD18). Each of these receptors serves a unique function in complement mediated immune response, and so agents designed to antagonize each of these receptors have unique therapeutic benefits. Indeed, a genetically engineered, soluble form of CR1, lacking transmembrane and cytoplasmic domains, has been tested as an anti-inflammatory agent and found to limit tissue injury in an in vivo model of acute inflammation. Another strategy for treating inflammatory disorders is to interfere with complement receptor 3 (CR3, CD18/11b)— mediated adhesion of inflammatory cells to the vascular endothelium. Experimental therapies which target complement receptor function also include the administration of CR3-specific antibodies which interfere with receptor-mediated adhesion of inflammatory cells to the vascular endothelium (Kirschfink, M. et al. (1997) Immunopharmacology (Netherlands) 38: 51–62). Such studies have demonstrated that protection against complement-mediated inflammatory tissue damage can be achieved using complement receptor antagonists in various animal models of sepsis, myocardial as well as intestinal ischemia/reperfusion injury, adult respiratory distress syndrome, nephritis and graft rejection. Thus complement receptor antagonists are suitable therapeutic agents to control inflammatory diseases and inflammatory related conditions.

Cell surface receptors have also been implicated in the genesis of cancer through the molecular analysis of the etiology of this group of related diseases characterized by a loss of cellular growth control. Indeed, cell surface receptors play multiple roles in oncogenic transformation including: serving as portholes for cellular infection by known and suspected human tumor viruses including Epstein-Barr virus, human T-cell leukemia virus (HTLV), Hepatitis B virus, and Papilloma viruses; serving as mediators of growth factor and transforming growth factor dependent stimulation of cancer cell growth through autocrine or paracrine mechanisms; and, finally, by indirectly facilitating the progression of cancer by potentiating the vascularization of tumor tissue and thus allowing for the continued growth of a mass of oncogenically transformed cells. Therapeutic agents capable of blocking any or all of these receptor functions thus have great utility in the treatment and prevention of human cancers. For example, the mitogenic action of epidermal growth factor (EGF) is mediated by ligand-induced autophosphorylation of the EGF receptor (EGFR), and EGFR is commonly overexpressed in solid human tumors. Compounds designed to block receptor tyrosine kinase activity by serving as competitive inhibitors of ATP binding to the intracellular kinase catalytic domain of the EGFR, have been shown in cell culture studies to be capable of blocking EGF-stimulated growth in a concentration dependent manner without affecting basal growth (Wakeling et al. (1996) Breast Cancer Res. Treat. (Netherlands) 38: 67–73; see also Rewcastle et al. (1998) J. Med. Chem. 41:742–51). Furthermore, a broad spectrum neuropeptide receptor antagonist has been shown to inhibit tyrosine kinase activation, block cell growth and increase apoptosis in in vitro and in vivo studies of a small cell lung cancer in which cell growth is sustained by multiple autocrine and paracrine growth loops involving bombesin-like neuropeptide growth factors (Tallett, et al. (1996) Cancer Res. 56: 4255–63). Indeed, for certain cancers generally unaffected by conventional chemotherapeutics, such as colorectal cacrcinomas, the targeting of growth factor receptors appears to be a logical approach to designing effective treatments (reviewed in Normanno et al. (1998) Cancer Detect. Prev. 22: 62–7).

In another example of the involvement of cell surface receptors in human cancer, paracrine signaling by interleukin 1 (IL-1) and tumor necrosis factor (TNF) is known to trigger the proliferation of human cervical carcinoma-derived epithelial cells and this process is mediated by an induced autocrine interaction of secreted amphiregulin with EGFR. In this system a number of different receptor antagonists, including an IL-1 receptor antagonist, soluble TNF type 1 or 2 receptor extracellular. domains, or EGFR monoclonal antibodies, prevented mitogenic stimulation (Woodworth et al. (1995) Proc. Natl. Acad. Sci. U.S.A. 92: 2840–4). These results demonstrate that cell surface receptors responding to both paracrine and autocrine signals are involved in oncogenic transformation and, furthermore, that receptor antagonists targeting either type of growth factor signaling can serve as effective oncogenic growth inhibitors. Similarly, dopamine receptor antagonists inhibited the growth of human small cell lung cancer in tumor implanted athymic nude mice (Ishibashi et al. (1994) Cancer Res. 54: 3442–6); and steroid receptor antagonists have proven valuable in the treatment of certain androgen-dependent cancers (reviewed in Wakeling (1992) Cancer Surv. (United States) 14: 71–85).

Furthermore, later stages in tumor establishment and metastasis are also potential targets for receptor antagonist therapeutics. For example, recent studies on angiogenesis in human solid tumors have suggested that inhibiting the function of vascular endothelial growth factor (VEGF) receptors and basic fibroblast growth factor (bFGF) receptor would prove effective in blocking neovascularization in a variety of tumor types (reviewed in Toi et al. (1998) Gan To Kagaku Ryoho (Japan) 24: 2202–6). In addition, the urokinase plasminogen activator (uPA) and its receptor are essential mediators of such metastatic functions as extracellular matrix proteolysis and tumor cell migration and small molecule antagonists of the uPA receptor promise to serve as useful adjuvants in combination with existing chemotherapy strategies (Ignar, et al. (1998) Clin. Exp. Metastasis (England) 16: 9–20). Thus it is clear that receptor antagonists can inhibit the initiation and progression of cancer by blocking any of a number of processes involved in oncogenic transformation and growth. Indeed the use of receptor antagonists has even proven fruitful in the prevention of nausea and emesis (vomiting) in cancer patients undergoing chemotherapy. In particular, antagonists of the 5-hydroxytryptamine 3-receptor have proven effective toward this goal (Perez et al. (1998) Cancer J. Sci. Am. 4: 52–8).

The utility of cell receptor antagonists is not limited to the treatment of cancers and inflammatory diseases. For example, many examples of pharmacologically active receptor antagonist compounds exist in the art. Cell surface receptors on neurons mediate neurotransmitter signaling and so neurotransmitter receptor antagonists have applications in treating neurological diseases and conditions as well mental and emotional disorders. For example, recent evidence suggests that Parkinson's disease is principally a glutamate hyperactivity disorder and hence treatable with glutamate receptor antagonists (reviewed in Starr (1995) Synapse 19: 264–93). And the usefulness of neurotransmitter receptor antagonists in treating mental and emotional conditions is also well established—for example the use of tricyclic muscarinic receptor antagonist compounds like lofepramine to treat depression (reviewed in Leonard (1987) Int. Clin. Psychopharmacol. (England) 2: 281–97). Furthermore, receptor antagonists have been used successfully to treat neuroendocrine disorders such as in the case of hyperthyroidism treatments employing beta-blocker compounds which antagonize the beta-receptor mediated effects of catecholamines (reviewed in Geffner and Mershman (1992) Am. J. Med. 93: 61–8).

Still other examples of receptor antagonists which are useful as therapeutic agents include angiotensin II receptor antagonists. Interruption of the renin-angiotensin-aldosterone system by such compounds has been shown to dramatically reduce renal damage in a renal hypertensive disease model (reviewed in Ibrahim, et al. (1998) Semin. Nephrol. 17: 431–40). Examples of widely used therapeutic receptor antagonists include histamine 2 receptor-antagonists which are sold over-the-counter for use in treating acid peptic disorders including gastric ulcers, duodenal ulcers, and gastroesophageal influx disease (Sanders (1996) Clin. Ther. 18: 2–34).

Receptor antagonists are also capable of altering the ability of infectious agents such as viruses and microbes (including pathogenic bacteria and fungi) to recognize and utilize host cell surface receptors. Indeed, as mentioned earlier, there are several examples of tissue-tropic tumor causing viruses, including human T-cell leukemia virus (HTLV), Epstein-Barr virus, hepatitis B virus and various human papillomaviruses, which are known or suspected of using specific host cell surface receptors as portholes of entry into a host cell. Significantly, another well examined virus, HIV (Human Immunodeficiency Virus), also frequently results in cancer in the afflicted individual. In the case of HIV, however, cancer is thought to result indirectly from, for example, the virus's weakening of the immune system, leaving the patient susceptible to viruses such as the above-mentioned tumor-causing Epstein-Barr virus. Indeed, infection by HIV also frequently leads to acquired immunodeficiency syndrome (AIDS), which commonly includes the development of Kaposi's sarcoma—a type of tumor which may be induced by growth factors released by HIV-infected cells. Thus appropriate receptor antagonists which target either the cell surface receptors implicated in HIV host cell infection or other cell surface receptors involved in the progression of AIDS (e.g. these receptors responding to Kaposi's sarcoma-associated secreted growth factors), would provide valuable therapeutic benefits in preventing HIV infection and treating AIDS.

Indeed, due to the public health concern and ensuing intense research, much is known about the mechanism by which HIV exploits host receptors to gain entry into a target cell. HIV-1 and related viruses possess a virion envelope glycoprotein (gp 120/41) which interacts with at least two cellular receptors: The CD4 molecule and a seven-transmembrane domain G-protein coupled chemokine receptor (D'Souza M. P. and Harden V. A. (1996) Nature Med. 2: 1293–1300). Macrophage-tropic (M-tropic) strains of HIV-1 replicate in macrophages and $CD4^+$ T cells and use the CC chemokine receptor CCR5 (Dragic, T. et al. (1996) Nature 381: 667–73; Deng, H. et al. (1996) Nature 381: 661–6; Alkhatib, G. et al. (1996) Science 272: 1955–8; Doranz, G. J. et al. (1996) Cell 85: 1149–58; Choe, H. et al. (1996) Cell 85: 1135–48). These HIV-1 viruses can be classified as R5 type based on their co-receptor usage (Berger, H. A. et al. (1998) Nature 391:240). The CCR5 co-receptor is used by almost all primary HIV-1 isolates regardless of viral genetic subtype, and by the related lentiviruses HIV-2 (Berger, H. A. et al. (1998) Nature 391: 240) and simian immunodeficiency virus (SIV) (Edinger, A. L. et al. (1997) Proc. Natl. Acad. Sci. USA 94: 4005–10). T-tropic isolates of HIV-1 replicate in primary $CD4^+$ T cells, as well as established $CD4^+$ T cell lines and macrophages. All of these viruses use the CXC chemokine receptor CXCR4, and many of them also use CCR5 (Feng, Y. et al. (1996) Science 272: 872–7; Simmons, G. et al. (1996) J. Virol. 70: 8355–60; and Connor, R. I. (1997) J. Exp. Med. 185: 621–8). Those viruses that only use CXCR4 are referred to as X4, whereas viruses that use both receptors with comparable efficiency are referred to as R5X4 (Berger, H. A. et al. (1998) Nature 391: 240). Although CCR5 and CXCR4 are believed to be the primary receptors for entry of HIV-1, nine additional chemokine receptors, including one encoded by cytomegalovirus have been shown by in vitro assays to serve as co-receptors for HIV and SIV. Within the human genome, there exist approximately fifty additional open reading frames with sequence similarity to chemokine receptors; some of these may ultimately contribute to the growing list of chemokine receptors with HIV co-receptor activity (Cairns, J. S. and D'Souza, M. (1998) Nature Med. 4:563–8).

Several strategies have been devised to interfere with the progression of HIV-1 infection by preventing the expression or function of chemokine receptors. Such treatments include those employing administration of $CD4^+$T cells which have been treated with antibodies to induce down-regulation of CCR5 expression and those employing genetic manipulation of host cells so that they express protective genes which interfere with cytokine receptor protein expression or localization. Examples of protective genes of the latter example include those encoding genetically engineered ribozymes designed to recognize and cleave cytokine-encoding mRNAs, those encoding intrabodies or intracellular antibodies designed to bind to chemokine receptors and interfere with their expression, and those encoding intrakines which are secretion-defective forms of natural cytokines which remain intracellular and bind to newly synthesized cytokine receptor proteins and trap them in the endoplasmic reticulum where they are rapidly degraded. Other strategies have been devised to interfere with the extracellular recognition of the HIV-1 virion gp120, as opposed to the cell surface expression, of cytokine receptors. For example, monoclonal antibodies have been developed to target chemokine receptors. The first such reagent was 12G5, a murine mAb against the CXCR4 receptor (Endres, et al. (1997) Cell 87:745–56). Of the mAb to CCR5, one particular murine mAb designate 2D7, completely blocked the binding and chemotaxis mediated by the chemokines RANTES, MIP-1α, and MIP-1β, This mAb also efficiently blocked the infectivity of several R5 and R5X4 viruses. Mapping studies have revealed that 2D7 maps to the second extracellular loop of CCR5, an important domain for both gp120 and chemokine binding (Wu et al. (1997) J. Exp. Med. 186: 1373–81). However, the development of mAbs for use as anti-HIV therapeutics is still subject to several obstacles including the high cost of production of these reagents, accessibility of the targeted cell population, and the possible immunogenicity of the mAb.

Another strategy for blocking HIV-1 infection has been to utilize natural chemokine receptor ligands which have been shown to compete with HIV-1 envelope glycoprotein for binding to HIV-1 chemokine coreceptors in certain instances. For example, experimental cell culture studies have demonstrated that RANTES, MIP-1a, and MIP-1b can inhibit the replication of R5 viruses, the CCR5 chemokine-utilizing subclass of HIV-1 viruses (Cocchi et al. (1995) Science 270: 1811–5). Similarly, the chemokine SDF-1 has been shown to competitively block viral entry of X4 viruses (Bleul et al. (1996) Nature 382: 829–33; Oberlin et al. (1996) Nature 382: 833–5). Other recently described CC chemokines with anti-viral properties include 1–309 the ligand for CCR8 (Tiffany et al. (1997) J. Exp. Med. 186: 165–70) and macrophage-derived chemokine (MDC) which exhibits a broad range of suppressive activity against diverse primate lentiviruses (Pal et al. (1997) Science 278: 695–8).

Several studies are planned or at the proof-of-concept stage using biologically active or inactive variants of these molecules. One such agent that has already been tested in the clinic is a variant of the CCR5-binding chemokine MIP-1α, called BB-10010. In a phase I study of BB10010, no consistent changes were noted in viral load, CD4 counts, or HIV isolate co-receptor usage. This is the predicted result considering the median plasma concentration of BB-10010 was only 3.5 ng/ml after six days of treatment, much lower than the 90–900 ng/ml range required to see antiviral effects of chemokines in vitro. In the absence of innovative dosing strategies to improve the efficacy of BB-10010, this ligand is unlikely to succeed in the clinic.

Therapeutic interventions based on administration of chemokines or over expression of these bioactive compounds are also compromised because of the key role these molecules play in inflammation. Furthermore, other in vitro observations also complicate the therapeutic use of chemokines. One overriding concern is the observation that in certain circumstances, the β-chemokines administered alone can actually enhance the replication of X4 HIV-1 isolates (Trikola, et al. (1998) J. Virol. 72: 396–404). Similarly, SDF-1, has been found to stimulate certain R5 HIV-1 isolates (Trikola, et al. (1998) J. Virol. 72: 396–404). In both of these instances, the stimulatory effect seems to depend upon the ability of the chemokine to transmit intracellular signals to the target cell following interaction with its receptor on the target cell membrane. Thus compounds which possess the HIV-1 gp120 blocking activity of these chemokines, but which do not possess their ability to activate the chemokine receptor signal transduction cascade resulting in undesirable HIV-1 replication enhancement, would obviously be preferable as a therapeutic. A second concern is that under certain circumstances, MIP-1α, MIP-1β, and RANTES, when administered alone, can enhance (Schmidtmayerova et al. (1996) 382: 767) CCR5-mediated fusion, entry and replication of R5 strains in macrophages, in contrast to their inhibitory properties in T cells. Because macrophages are likely to be among the first cells exposed to HIV and constitute a reservoir for the virus, these observations engender caution, and suggest again a need for therapeutics which retain the ability to block HIV-1 gp120 interaction with the chemokine receptor, yet which do not possess the abovementioned undesirable activities.

Modified β-chemokines that block HIV infection without inflammatory side effects or the HIV-1-stimulatory effects of the parent molecules are second generation compounds with such therapeutic promise. Two β-chemokine derivatives that bind CCR5 and lack cellular signaling capabilities are under investigation: RANTES(9–68), a truncated form of RANTES (Arenzana-Seisdedos et al. (1996) Nature 383: 400); and aminooxypentane (AOP)-RANTES, a version that is chemically modified at the amino terminus (Simmons, et al. (1997) Science 276:276–9). Both of these compounds exhibit increased potency when compared to RANTES and inhibit the infection of primary lymphocytes by R5 viruses in tissue culture experiments without stimulating X4 subclass HIV-1 replication. AOP-RANTES was also able to inhibit replication of R5 strains in primary human macrophages. Although the unmodified β-chemokines block HIV infection of dendritic cells (Granelli-Piperno et al. (1996) J. Exp. Med. 184: 2433–8), the inhibitory properties of these modified chemokines on dendritic cells and other sites of viral entry remain unknown. Two peptides that appear to block the CXCR4-HIV interaction are T22 (Murakami et al. (1997) J. Exp. Med. 186: 1389–93) and ALX40-4C (Doranz et al. (1997) J. Exp. Med. 186: 1395–1400). T22 is an 18-amino acid peptide derived from the hemocyte debris of the horseshoe crab. It blocks membrane fusion and infection by X4 type HIV-1 viruses as well as chemotaxis in response to SDF-1. ALX40–4C is a highly cationic peptide containing nine arginines. This compound also blocks HIV envelope interactions and SDF-1 interaction with CXCR4.

While these natural and synthetic chemokine-related compounds show some promise as anti-HIV therapeutics, their practical use presents several difficulties. In particular, such peptides in general are of uncertain stability in the bloodstream, and chemokines, in particular, are thought to possess a relatively short half-life in circulation (<10 minutes) (Van Zee et al. (1992) J. Immunol. 148: 1746–52). At least one limitation to chemokine serum half-life appears to be their propensity for binding to cell surface proteoglycans as well as other glycosaminoglycans present in intercellular and extracellular matrices. This tendency reflects the apparent use by chemokines of heparan sulfate proteoglycans to promote efficient binding to chemokine receptors and to thereby promote the anti-viral activity of chemokines in cell culture experiments (Oravecz, et al. (1997) J. Immunol. 159: 4587–92). Furthermore, recent studies suggest that HIV-suppressive chemokines produces by $CD8^+$ T cells (Cocchi, et al. (1995) Science 270: 1811–15) are secreted in a form complexed to proteoglycans (Wagner et al. (1998) Nature 391: 908–11).

As summarized above, the ability to block the function of a receptor with a receptor antagonist provides a means of specifically interfering with the molecular processes underlying many diseases, conditions, and infectious states. Nevertheless, several obstacles remain to the development of effective receptor antagonist therapeutics for treating inflammatory disorders, cancers, infections and other diseases and conditions whose etiology involves the function of a cell surface receptor. In particular many of the above-described receptor antagonists, while practical as experimental reagents for investigating the potential utility of targeting a particular receptor, are inappropriate as pharmaceutical therapeutics for various reasons such as poor solubility, toxicity, short serum half-life, or undesirable side effects. For example, although the initial laboratory data on the ability of the above-described natural and altered chemokine and chemokine derivative peptides to block the interaction of HIV envelope with chemokine receptors may be encouraging, the therapeutic potential of these compounds administered alone is uncertain owing to a number of likely problems confronting their use in vivo. In particular, the abovementioned problem of the short serum half-life of exogenously administered chemokines needs to be addressed. Another major problem with using chemokines as anti-HIV therapeutics is their previously mentioned tendency to increase viral replication under certain circumstances. Yet another problem with this potential HIV therapeutic is the occurrence of undesirable side-effects owing to the continued activation of chemokine responsive cells. Within the anticipated time frame required to effectively lower viral loads using such a treatment strategy, such chronic stimulation of the immune system would create additional medical complications for the HIV infected patient.

Furthermore, the development of effective receptor antagonist compounds for treating the abovementioned diseases and conditions is frequently limited by the complicated bioassays utilized to study such processes. Indeed such assays often preclude the use of high-throughput screening techniques to identify appropriate receptor antagonists compounds. Furthermore, antagonists identified through such techniques must undergo further in vivo screening to characterize adverse side effects and to minimize toxicity. Rational design strategies offer a solution to at least the first and frequently the second cited problem of developing receptor antagonist therapeutics. Unfortunately most rational design strategies require detailed knowledge of the structure of the therapeutic target. However the detailed three dimensional structure, as determined by X-ray crystallographic analysis, is frequently not available for such cell surface receptors—at least in part owing to the difficulty in obtaining adequate crystals from lipophilic membrane proteins.

There is thus a great need for methods of formulating effective receptor antagonists based upon rational design concepts that do not require extensive screening.

2. SUMMARY OF THE INVENTION

The present invention affords a solution to this and other problems confronting the developer of suitable receptor-targeting therapeutics. In particular, in one aspect, the present invention provides for the facile modification of known receptor ligands with ligand binding molecules to form therapeutic receptor ligand-containing antagonist complexes. The invention thus allows for facile conversion of natural receptor agonists into novel pharmaceutical formulations which act as receptor antagonists.

Preferred receptor ligands are natural or synthetic molecules that bind to receptors involved with disease causing ligand/receptor-mediated signaling pathways or which are involved with extracellular recognition of an infectious agent. Examples of such receptors include: chemokine coreceptors, which mediate host cell uptake of viruses such as HIV, growth factors, which are associated with the development of certain cancers, and complement receptors, which are associated with the development of certain inflammatory diseases. Examples of preferred receptor ligands include: chemokines and receptor binding portions thereof; growth factors; and complement proteins. Particularly preferred chemokine ligands include interleukins, tumor necrosis factors, lymphokines, interferons and lymphotoxins. In a preferred embodiment, the chemokine is MIP-1α, MIP-1β, RANTES, MDC, I-309, eotaxin, MCP-3, or SDF-1.

Preferably the receptor ligand binding molecule is a natural or synthetic molecule that specifically binds the ligand, but is not the receptor or a fragment thereof. Examples of preferred receptor ligand binding molecules include polyanionic compounds, such as glycosaminoglycan. Preferred glycosaminoglycans are heparan, heparan sulfate, chondroitin sulfate, or dermatan sulfate. In yet another embodiment of the basic method of the invention, the receptor ligand and the receptor ligand binding molecule are noncovalently associated prior to administration to the patient to be treated. In other embodiments of the invention, the receptor ligand and the receptor ligand molecule are covalently associated prior to administration to the patient. In preferred embodiments, the composition resulting from combination of the receptor ligand and the receptor ligand binding molecule has a longer half-life than that of the receptor ligand alone.

Given their novel properties, receptor ligands in association with receptor ligand binding molecules should prove to be effective therapeutics. In addition, since the complexes are unable to trigger receptors, they should prove to be free from undesirable side effects resulting from the continued activation of their target receptor as has been observed in the use of chemokines to block HIV infection. Moreover, such complexes are unlikely to be deposited on irrelevant extracellular surfaces and therefore should specifically localize at appropriate in vivo locations to mediate a prophylactic or therapeutic effect.

In another aspect, the invention features novel methods for treating diseases or conditions, which are caused by or contributed to by the function of a ligand/receptor-mediated signaling pathway or which are dependent upon the extracellular recognition of a receptor by an infectious agent based on administration to a subject of a therapeutically effective amount of a receptor ligand and a receptor ligand binding molecule, wherein the receptor ligand and receptor ligand binding molecule are complexed or are capable of complexing in vivo, thereby antagonizing the function of the receptor or altering the extracellular recognition of the receptor by the infectious agent, resulting in treatment of the disease or condition.

In certain embodiments of the present invention, the disease or condition is dependent upon the extracellular recognition of a receptor by an infectious agent. In preferred embodiments, the infectious agent is a virus selected from the group comprising: an Human Immunodeficiency Virus such as HIV-1, an Epstein-Barr Virus, a Rhinovirus, a Poliovirus, a Rabies Virus, a Reovirus, an Influenza Virus, an Herpes Simplex Virus, an Hepatitis virus, a Togavirus, a Varicella-Zoster Virus, a Paramyxovirus, a Cytomegalovirus, a Subacute Sclerosing Panencephalitis Virus, an Adenovirus, a Poxvirus, a Reovirus, a Papovavirus, a Papillomavirus, a Polyomavirus, and a Slow virus.

In another embodiment, the infectious agent is a microbe which requires a specific host receptor or receptors for colonization or penetration. In preferred embodiments, the microbe is a bacterium selected from the group comprising: *Helicobacter pyloris, Borelia burgdorferi, Legionella pneumophilia, Mycobacterium tuberculosis, Mycobacterium avium, Mycobacterium intracellulare, Mycobacterium kansaii, Mycobacterium gordonae, Mycobacterium leprae, Staphylococcus aureus, Neisseria gonorrhoeae, Neisseria meningitidis. Listeria monocytogenes, Streptococcus pyogenes, Streptococcus agalactiae, Streptococcus faecalis, Streptococcus bovis, Streptococcus anginosus, Streptococcus pneumoniae*, pathogenic Campylobacter species, pathogenic Enterococcus species, *Haemophilus influenzae, Bacillus antracis, Corynebacterium diphtheriae, Erysipelothrix rhusiopathiae, Clostridium perfringers, Clostridium tetani, Enterobacter aerogenes, Klebsiella pneumoniae, Pasturella multocida*, pathogenic *Bacteroides fragilis* group species, *Fusobacterium nucleatum, Streptobacillus moniliformis, Treponema palladium, Treponema pertenue*, Leptospira, and *Actinomyces isrealli*. In yet other embodiments, the microbe is a fungus selected from the group comprising: *Cryptococcus neoformans, Histoplasma capsulatum, Coccidioides immitis, Blastomyces dermatidis, Chlamydia trachomatis*, and *Candida albicans*.

In further embodiments of the invention, the disease or condition is caused by or contributed to by the function of a ligand/receptor-mediated signaling pathway. In one preferred embodiment, the disease or condition is, an inflammatory or an immune disease or disorder. In another preferred embodiment, the disease or condition is a cancer.

In still a further aspect, the invention features screening assays for identifying therapeutically effective formulations of particular receptor ligand-containing antagonist complexes for use e.g. in treating and/or preventing the development of a disease or condition that is caused by or contributed to by the function of a cell surface receptor.

Other features and advantages of the invention will be apparent from the following detailed description and claims.

3. BRIEF DESCRIPTION OF THE FIGS.

Figure 3:
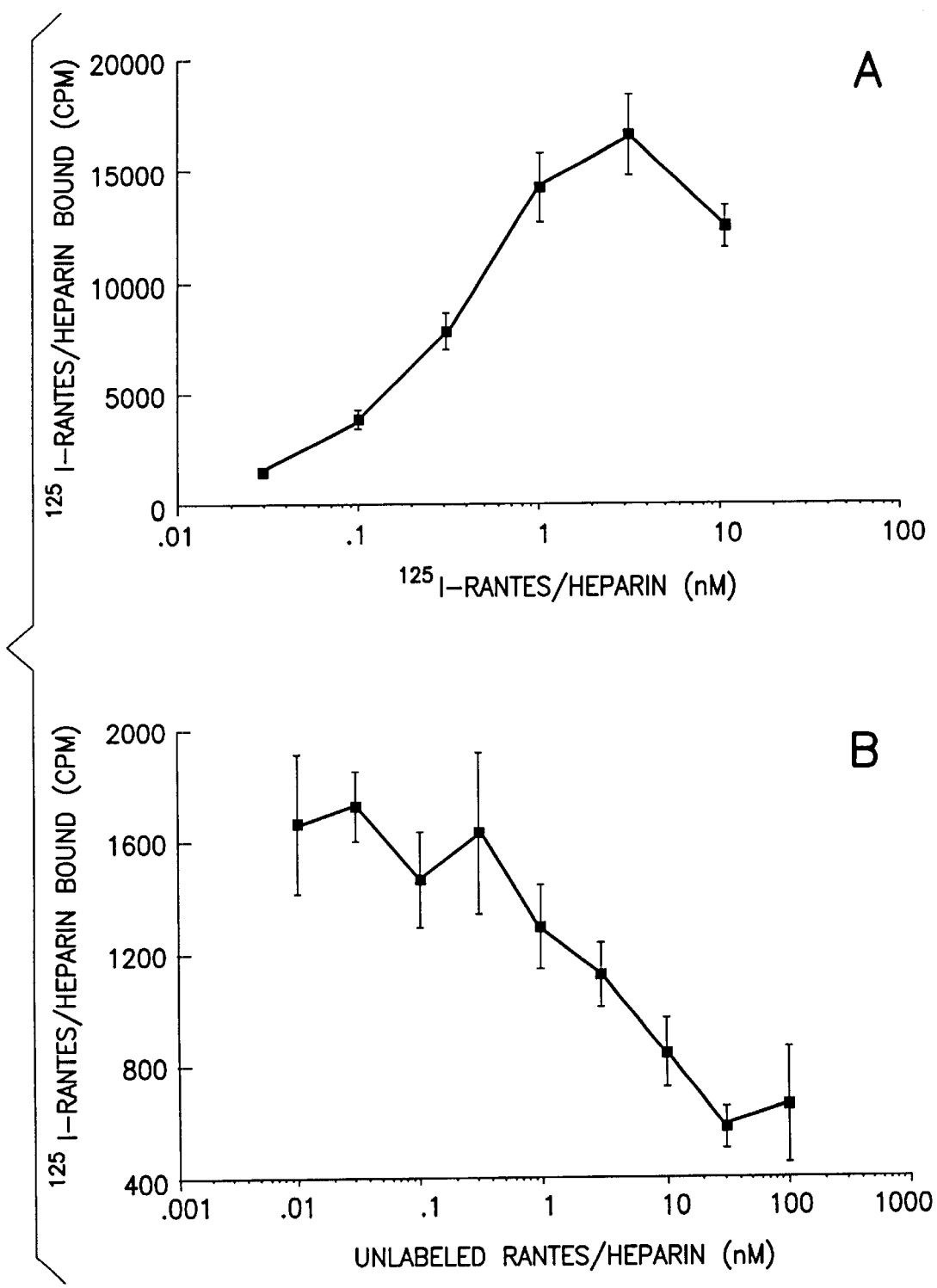

FIG. 3, Panel A is a graph which shows the binding of $^{125}$I-labeled RANTES-heparin complexes to glycanase treated PBMC. FIG. 3, Panel B shows that binding of RANTES-heparin complexes is specific—the binding of labeled chemokine-heparin complexes can be competed with unlabeled chemokine-heparin complexes.

Figure 4:
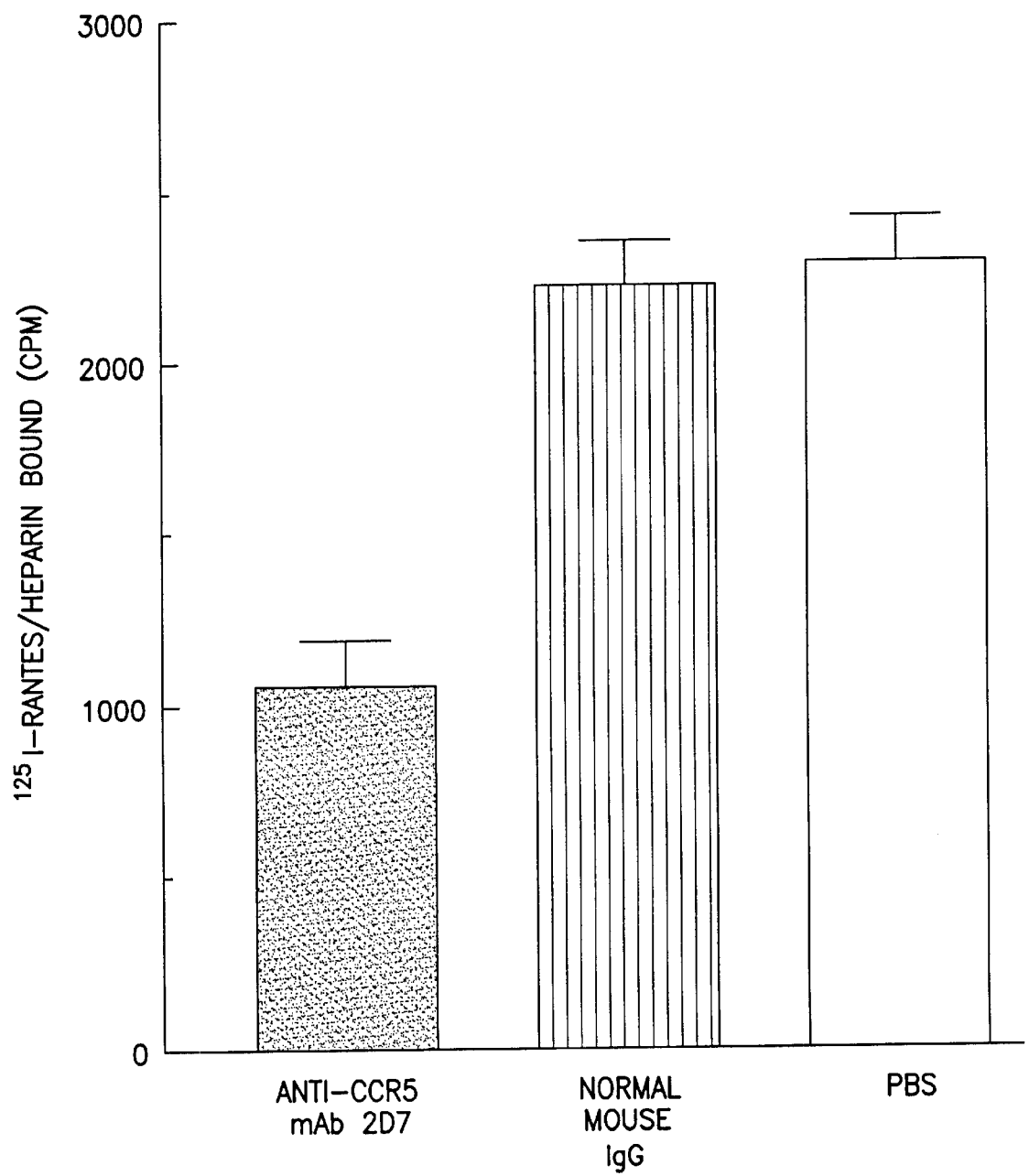

FIG. 4 is a bar graph showing the inhibition of $^{125}$I-labeled RANTES complex binding to glycanase treated PBMC by anti-CCR5 mAb 2D7.

Figure 5:
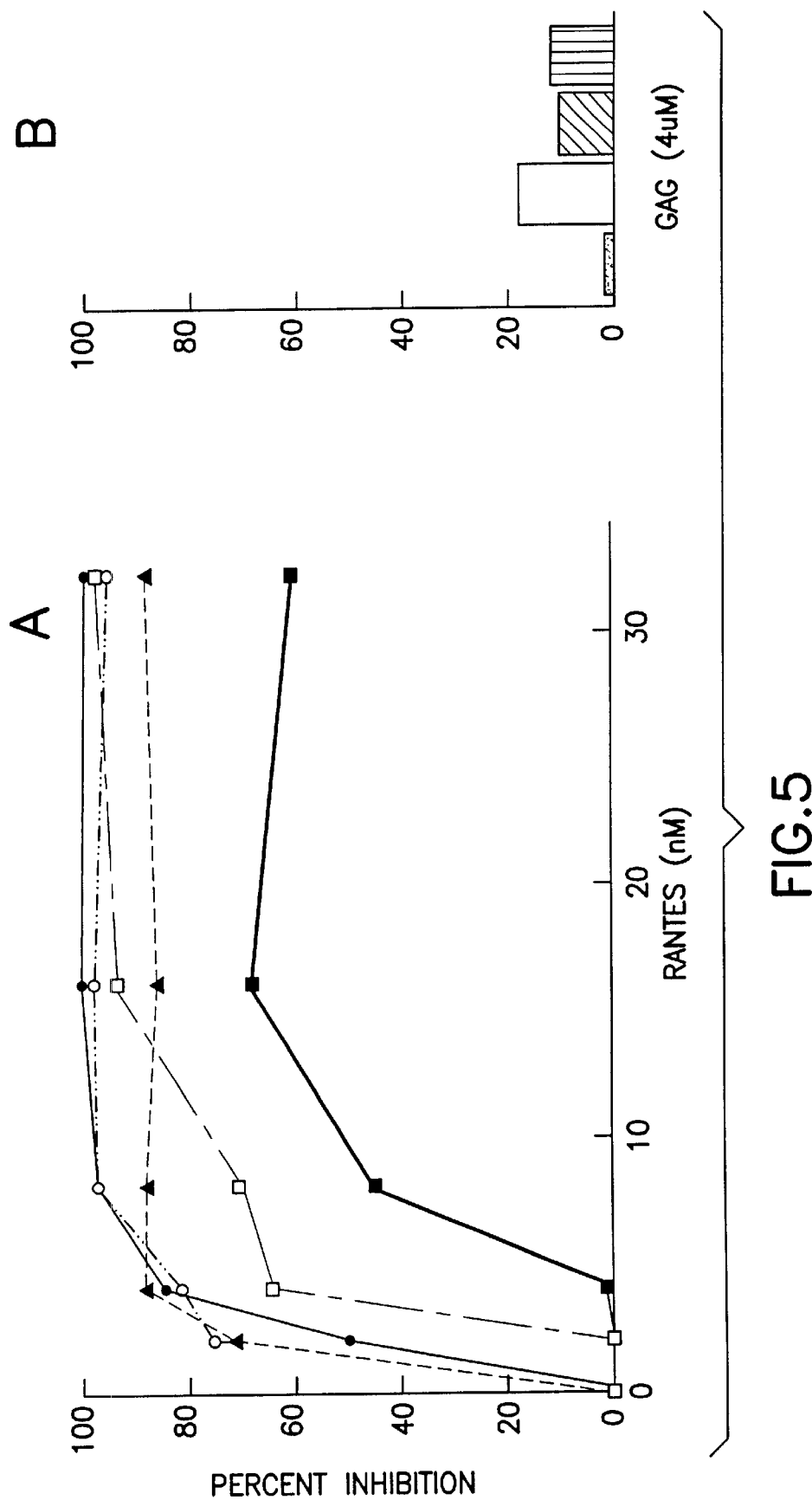

FIG. 5, Panel A is a graph showing the inhibition of HIV-1 replication in PM1 cells by RANTES complexed with GAGs. FIG. 5, Panel B is a bar graph showing the results of control experiments performed with sham formulations containing only heparin (black bar), heparan sulfate (open bar), chondroitin sulfate (diagonal striped bar) or dermatan sulfate (vertical striped bar) at a concentration matching the highest amount tested in the RANTES-GAG preparations (4 μM).

Figure 6:
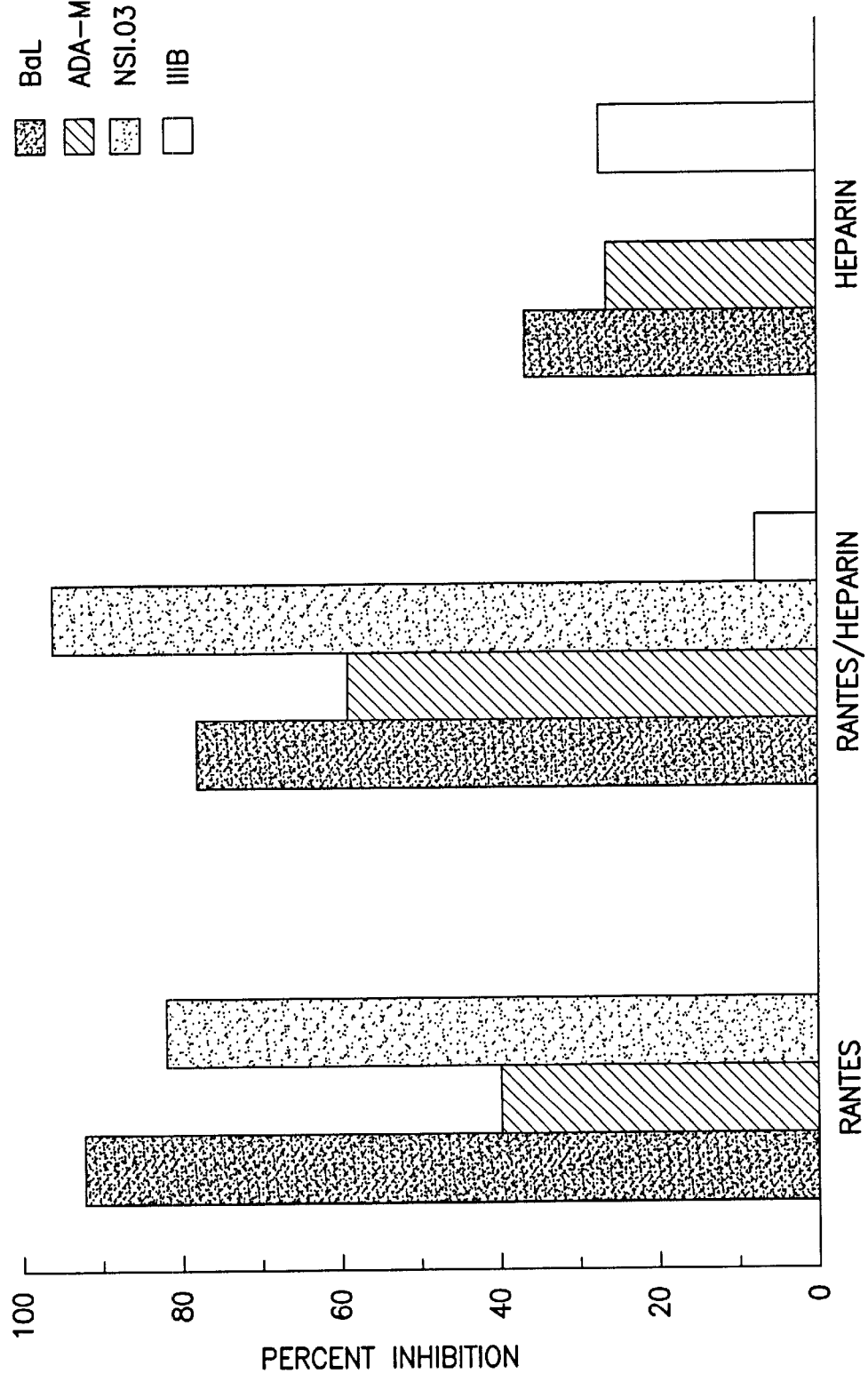

FIG. 6 is a bar graph showing the antiviral effects of RANTES-GAG complexes on primary macrophage-tropic HIV isolates which are CCR5 tropic (BaL, NSI.03, and ADA-M) versus HIV-$I_{IIIB}$.

Figure 7:
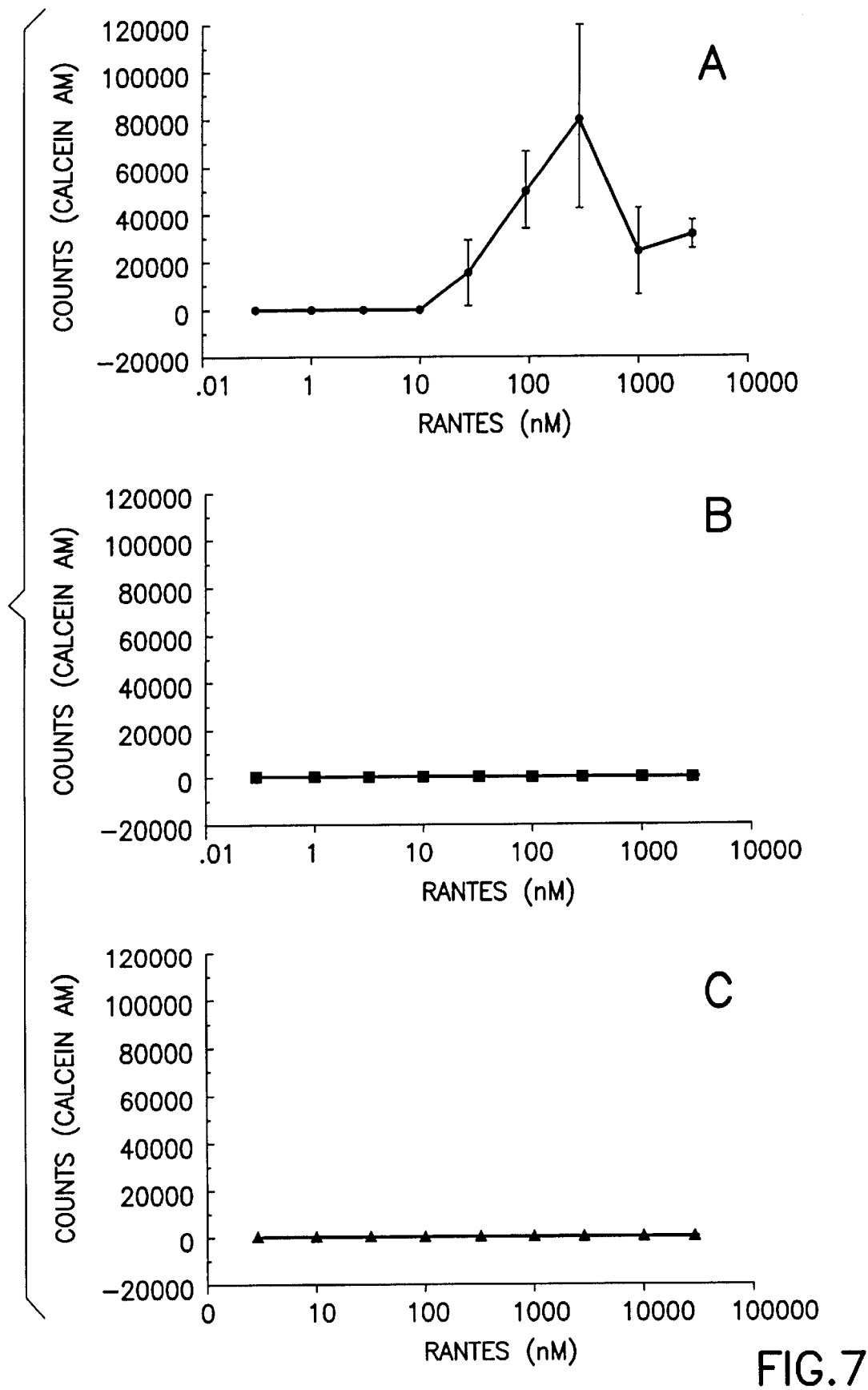

FIG. 7 shows the effects of the RANTES-heparin chemokine receptor antagonist complex upon chemotaxis in differentiated HL-60 cells. "Panel A shows the positive control (chemotactic response of HL-60 cells to RANTES);

Panel B shows that formation of a RANTES-heparin complex blocks RANTES-induced chemotaxis; and Panel C shows the negative control (chemotactic response of HL-60 cells to heparin alone).

4. DETAILED DESCRIPTION OF THE INVENTION

4.1 General

The instant invention is based, at least in part, on the surprising finding that chemokine-glycosaminoglycan complexes retain the ability of the chemokine to suppress HIV-1 infection, but do not trigger normal receptor signaling. Based on the similar extracellular recognition of a receptor by infectious agents other than HIV and the involvement of receptor-ligand mediated signaling pathways in many diseases and conditions, the invention features a variety of novel receptor ligand containing antagonists and their use in preventing and treating certain diseases.

4.2 Definitions

For convenience, the meaning of certain terms and phrases employed in the specification, examples, and appended claims are provided below.

The term "agonist," as used herein, is meant to refer to an agent that mimics or upregulates (e.g. potentiates or supplements) a receptor activity. A receptor agonist can be a wild-type protein or derivative thereof having at least one bioactivity of the wild-type receptor.

The term "AIDS" or "acquired immune deficiency syndrome," as used herein, is meant to refer to a condition of acquired immunological deficiency that is associated with infection of the cells of the immune system with the retrovirus HTLV-III and that is usually recognized by the presence of a life-threatening infection (as pneumonia or candidiasis) or of Kaposi's sarcoma in individuals under 60 years of age who have not been subjected to immunosuppressive drugs or an immunosuppressive disease.

"Antagonist" as used herein is meant to refer to an agent that down regulates (e.g. suppresses or inhibits) a receptor activity. The antagonist can be a dominant negative form of a receptor ligand.

"Cancer" as used herein is meant to refer to a malignant tumor of potentially unlimited growth that expands locally by invasion and systemically by metastasis. Examples of human cancers include cancers of the lung (including small cell carcinoma of the lung) breast, brain, cervix, colon, bone, and prostate.

"Chemokine" a member of a family of low molecular weight proteins that play a critical role in inflammatory immune processes. These proteins mediate a wide variety of effects, including intracellular calcium mobilization, chemotaxis and cell activation, as a result of interactions with 7 transmembrane spanning, G protein coupled receptors. A subset of chemokines, beginning with RANTES, MIP-1α, MIP-1β, have been demonstrated to suppress infection by the human immunodeficiency virus type 1 (HIV-1)[Cocchi, 1996 #3]. These molecules bind receptors also required by HIV-1 for entry into susceptible host cells and thus suppress infection as a result of receptor-ligand interactions. Chemokine function is intimately related to interactions with glycosaminoglycans (GAG). Nascent chemokines are transported to cell surfaces as complexes with GAGs [Tanaka, 1996 #2; Wagner, 1998 #1] and protein receptor activation requires surface chemokine-GAG interactions [Guimond, 1993 #8; Luster, 1995 #4]. In addition, chemokines are bound to GAGs on endothelial cell surfaces in order to form a concentration gradient thought to be critical for lymphocyte trafficking and inflammatory processes [Tanaka, 1993 #17; Tanaka, 1993 #16; Butcher, 1991 #15]. GAG interactions are also important for the antiviral activities of certain βchemokines. The binding of RANTES to heparan sulfate enhances the ability of this chemokine to block HIV infection [Wagner, 1998 #1] and it has been shown that RANTES, MIP-1α and MIP-1β are released from $CD^{8+}$ T cells as a complex with GAGs and that the antiviral effects of the β chemokines on macrophages requires such chemokine-GAG complexes [Wagner, 1998 #1].

The term "glycosaminoglycan" or (GAG) refers to naturally-occurring carbohydrate-based molecules implicated in regulation of a number of cellular processes, Including blood coagulation, angiogenesis, tumor growth, nerve cell development, smooth muscle cell proliferation, and gene expression, most likely by interaction with effector molecules (e.g. receptor ligands). GAG's are linear, non-branched chains of repeating two-sugar (disaccharide) units which maybe up to 150 units in length, and are well known and described in the art. See, for example, Jackson et al (1991) Physiological Reviews 71':481–539 and Kjellen et al. (1991) Ann. Rev. Biochem. 60:443–475. GAG's are often, but not always, found covalently bound to protein cores in structures called proteoglycans. Proteoglycan structures are abundant on cell surfaces and are associated with the extracellular matrix around cells. Chemically, glycosaminoglycans are typically composed of repeating disaccharide units where one of the monosaccharide units is a uronic acid and the other is either an N-acetylglycosamine or an N-acetylgalactosamine. The term "glycosaminoglycan", as used herein is further meant to describe any of a number of known mucosaccharide compounds such as heparin, heparan sulfate, chondroitin or dermatan sulfate, keratan sulfate, and hyaluronic acid. The term "glycosaminoglycan" is further meant to encompass synthetic polysaccharide compounds having binding specificity for proteins, including proteins that act as effectors of biological activity. Methods for identifying such synthetic oligosaccharides have been described (see PCT WO 94/20512).

The term "half-life" refers to the time required for half of a molecule to undergo a process: the time required for half the amount of a substance (as a drug or radioactive tracer) in or introduced into a living system or ecosystem to be eliminated or disintegrated by natural processes (the serum is about two days).

The term "heparin sulfate" as used herein is meant to refer to any of a number of chemically related sulfated mucopolysaccharides or mucopoysaccharide sulfuric acid esters. The term "heparin sulfate" as used herein is also meant to connote members of a large family of cell surface heparan sulfate proteoglycans. Both free heparin sulfate and the cell surface heparan sulfate proteoglycans are capable of serving the related function of facilitating receptor binding to any of a number of high-affinity receptors as defined above.

The term "infectious disease" refers to a disease caused by the entrance into the body of organisms (as bacteria, protozoans, fungi, or viruses) which grow and multiply there.

The term "inflammation" refers to a local response to cellular injury that is marked by capillary dilation, leukocytic infiltration, redness, heat, pain swelling, and often loss of function and that serves as a mechanism initiating the elimination of noxious agents and of damaged tissue.

The term "poly-anionic molecule" generally refers to a negatively charged polymer (i.e. a polymer that has at least two negative charges). Preferably for use herein, the polyanionic compound is biocompatible. Examples include proteins possessing negative charge, such as negatively charged albumins (NCA), sulfated polysaccharides such as glycosaminoglycans, and nucleic acid, such as ribonucleic acid or deoxyribonucleic acid.

The term "receptor" refers to a cell or group of cells that receives stimuli; a chemical group or molecule in a plasma membrane or cell interior that has an affinity for a specific chemical group, molecule, or virus; a cellular entity that is a postulated intermediary between a chemical agent (as a neurohormone) acting on a nervous tissue and the physiological or pharmacological response.

A "subject" can include mammals such as humans, rodents, non-human primates, sheep, dogs, cats, cows, chickens, amphibians, reptiles, etc.

The term "treating" as used herein is intended to encompass curing as well as ameliorating at least one symptom of the condition or disease.

4.3.1. Pharmaceutical Compositions

Chemical formulations comprising a receptor ligand and a receptor ligand binding molecule alone or in combination can be prepared and administered as described herein to treat or prevent a disease. The rational design of the pharmaceutical composition of the present invention thus requires the diligent selection of both an appropriate receptor ligand and an appropriate receptor ligand binding molecule. The two components of the pharmaceutical composition are described in detail below.

4.3.1.1 Receptor Ligands

The choice of a receptor ligand for use in preferred pharmaceutical compositions of the immediate invention will be informed by the nature of the disease, condition, or infection to be treated. Thus, in many instances, the disease to be treated will suggest a cell surface receptor whose function would be beneficially targeted such as those receptors involved in inflammatory disorders, cancer and HIV-1 infection as previously discussed. Still other conditions are also treatable using rationally designed formulations of the invention by simply incorporating a receptor agonist into the pharmaceutical formulation to arrive at a receptor antagonist. For example, since insulin is known to increase the rate of uptake of glucose from the blood into muscle cells and adipocytes, the incorporation of insulin into these pharmaceutical compositions may be useful in antagonizing insulin receptors and reversing insulin-dependent hypoglycemic conditions (e.g. "insulin shock"). In other instances, the choice of receptor ligand may be made in the absence of detailed knowledge regarding the cell surface receptor or receptors to be targeted based upon known biological effects of biologically active receptor ligands. For example, many pharmacologically active substances are known to act as receptor agonists and so incorporation of such compounds into the formulation of the present invention, would be expected to result in the effective conversion of a receptor agonist compound into a receptor antagonist. In still other instances, the choice of a receptor ligand may require the use of additional rational design studies. For example, in order to discover suitable receptor ligands for an "orphan" receptor (i.e. one for which no known physiological ligand exists). In particular, genetically dominant heritable diseases in humans which are determined by linkage, cloning, and sequence analysis, to correspond to alterations in an apparent cell surface receptor gene, are likely to correspond to diseases which result from the inappropriate continuous activation of the receptor concerned and hence would benefit from the receptor antagonist formulations of the present invention. In the case of such "orphan" receptors, the choice of suitable receptor ligand may be guided by the general class of receptors to which the disease receptor belongs (determined by sequence homology to the known receptors) and may further be guided by a combination of predictive computer algorithms for determining the three dimensional structure of the putative extracellular domain of the disease receptor, in conjunction with yet other algorithms designed to predict "best fit" ligands for a given protein structure (see, for example, PCT WO 95/18974).

In yet other instances where the pharmaceutical formulation of the present invention is used to treat an infection by a virus or a microbe, the choice of a receptor ligand will be guided by the known or suspected cell surface receptors utilized by the virus to gain entry into the cell or by the microbe to establish infection of a tissue or organ. For example many viruses that possess specific tissue tropisms, are. known or suspected of utilizing specific host receptor expressed on the surface of cells. of the targeted tissue in order to infect the target cell. Thus appropriate receptor ligands for treating these infections will be informed by the known or suspected viral receptor target.

The above examples describe some general situations and resulting considerations to be made when applying the method of the present invention to the treatment of a specific disease, condition, or infection. Further examples of choice receptor ligands for use in each of the above described situations, as well as in other situations encompassed by the method of the present invention, are discussed below.

In preferred inflammatory disorder therapeutics of the present invention, the receptor ligand is a chemokine such as MIP-1α, MIP-1β, RANTES, MDC, I-309, eotaxin, MCP-3, or SDF-1, and the pharmaceutical formulation resulting from incorporation of the chemokine antagonizes cell adhesion events involved in the inflammatory response (for example, T-cell, neutrophil, or monocyte adhesion). Most chemokines possess two major binding surfaces: a high affinity site responsible for specific ligand/receptor interactions and a lower affinity site, also called the heparin-binding or glycosaminoglycan-binding domain, believed to be responsible for the establishment and presentation of chemokine gradients on the surface of endothelial cells and within the extracellular matrix. Although chemokines are clearly beneficial in wound healing, hemopoiesis, and the clearance of infectious organisms, the continued expression of chemokines is associated with chronic inflammation. Therefore, this class of cytokines are attractive targets for the creation of antagonists that abrogate one or more chemokine functions. Such antagonists could serve as a new class of anti-inflammatory drugs.

In other embodiments, the invention utilizes cytokines which signal by are localized to the nucleus by means of ligand-induced endocytosis of cytokine-receptor complexes. Several cytokines or their receptors contain nuclear localization signals. Once internalized, these cytokine-receptor complexes may move into the nucleus. Proteins larger than 40–45 kDa enter the nucleus only by active transport through the nuclear pore complex (Johnson et al. (1998) biochem Biphys Res Comm 244: 607). Protein translocation requires the presence of a nuclear localization signal (NLS) that consists of two closely-spaced groups. A protein binds via its NLS to a complex called importin, which mediates docking to the nuclear pore complex and translocation across the nuclear envelope. Nuclear localization has been observed for several cytokines, including insulin, IFN-γ, IL-1, IL-5, PDGFs, growth hormone, and members of the FGF family. In some cases the NLS function has been confirmed by mutational analysis or by demonstration of the ability of the NLS to target a heterologous protein to the nucleus. IFN-γ is known to re rapidly translocated too the nucleus following receptor binding, and it contains an NLS (RKRKRSR) near its C-terminus that is essential for bioactivity. Furthermore, receptor-independent delivery of IFN-γ via microinjection or secretion-defective intracellular expression elicitys IFN-γ bioactivity. Further evidence of a distinct nuclear target for IFN-γ is provided by studies which demonstrate that human IFN-γ does not activate mouse cells when delivered exogenously because of an inability to bind to the mouse receptor, however direct microinjection of human IFN-γ into mouse macrophages does elicit bioactivity (Smith et al. (1990) J Immunol 144: 1777). Signaling by IFN-γ activates JAK-1 and JAK-2 kinases resulting in the phosphorylation of STAT-1 (Silvennoinene et al. (1997) APMIS 105: 497). Activated STAT-1 forms a homodimer that is translocated to the nucleus and serves to upregulate several genes. The STAT proteins have, however, no nuclear localization signals and suggesting that nuclear translocation of STAT-1 occurs while it is complexed with IFN-γ and the α chain of IFN-γR. A number of other cytokines also activate STAT proteins; in every case there is a putative NLS on either the cytokine or its receptor. Nuclear translocation requires the cytokine-receptor complex, but the role of these complexes within the nucleus is unknown. Cytokine-receptor complexes act as chaperones to accomplish a cytokine-specific nuclear translocation of activated STATs. These complexes might similarly chaperone other signaling molecules, such as kinases or transcription factors, that function withing the nucleus. Cytokines and/or receptors in complex with transcription factors might also provide secondary interactions that help discriminate between similar nuclear response elements within multiple promoters. Thus these nuclear targets of cytokine signaling provide another potential target for the receptor antagonist complexes of the present invention. For example IFN-γ/GAG complexes may block both IFN-γ activation and subsequent IFN-γ mediated activation of nuclear target genes.

In other embodiments, the invention features antagonist complexes that target the function of viral cytokine receptors. Many viruses encode "non-essential" genes, which are homologous to cellular genes, used by the virus to counteract the host immune response. These viral genes are thought to have been captured from the host cells during viral evolution and modified to confer an advantage in viral replication, survival or transmission. For example the myxoma virus produces a soluble IFN-γ receptor homologue, called M-T7, that can bind IFN-γ and inhibit its anti-viral activities. Also the presentation of viral antigen by the MHC class I molecule can be disrupted by adenoviral E3-gp19K and UL18 from human cytomegalovirus. Other soluble cell-receptor homologues include: myxoma virus, M-T2, a cellular TNF-receptor homologue that binds and inhibits TNF; B15R from the vaccinia virus, asecreted IL-1 recptor type II homologue that binds and inhibits the action of IL-1β; and E3-14.7K, E3-10.4/14.5K, and E1B-19K from adenovirus which block TNF action. Other viral proteins block host complement function by producing viral proteins that bind complement subunits and inhibit complement-mediated lysis of infected cells (e.g. Epstein Barr BCFR1, an IL-10 homologue). Some viral genomes have sequences homologous to those of chemokines and chemokine receptors. There are three chemokine receptor homologues, US28, US27 and UL33 in the cytomegalovirus genome. US28-transfected cells can bind a wide range of chemokines, includeing MCP-1, RANTES, and MIP-1α (Pleskoff et al. (1997) Science 276: 1874). Mutation of M33 had no effect on infection of mouse fibroblasts in vitro, but in vivo there was much less virus in the salivary glands of mice infected with the mutant than with wild-type virus. Therefore M33 could be important to the movement of virus through infected cells to the salivary glands to assist in viral transmission to new hosts (Davis-Poytner et al. (1997) J Virol 71: 1521).

Other examples of effective receptor ligands for use in treating inflammatory disease using the immediate pharmaceutical formulation include ligands known or suspected to act in the complement system. Thus, in some embodiments of the invention, the receptor ligand is a complement receptor binding protein or polypeptide such as complement fragment C3b, C4b, iC3b, C3dg, C3a, C4a, C5a, or C5a-des arg. In other embodiments, the receptor ligand is a molecule which binds to a complement receptor such as the complement receptor type 1 (also known as CR1, C3b receptor or CD35), complement receptor type 2 (also known as CR2, C3d receptor or CD21), or complement receptor type 3 (also known as MAC-1, CR3, or CD11bCD18). In preferred embodiments of the invention, the receptor ligand molecule mediates a biological function of the complement system such as complement-mediated cytolysis, opsonization and promotion of microbe phagocytosis, or solubilization and phagocytic clearance of immune complex. In still more preferred embodiments, the receptor ligand is an anaphylatoxin, preferably C3a, C4a, or C5a. In other preferred embodiments, the receptor ligand is a component of the complement system whose function or aberrant function causes of contributes to a disease or condition such as an inflammatory or an autoimmune disease. Such inflammatory or autoimmune diseases include complement deficiencies including systemic lupus erythematosus, glomerulopnephristis, vasculitis, pyogenic infections, immune complex disease, disseminated Neisserial infections, hereditary angioneurotic edema (HANE), paroxysmal nocturnal hemoglobinuria or a leukocyte adhesion deficiency. In still other embodiments the receptor ligand is a bradykinin or a peptide kinin that binds to a bradykinin receptor. In still other embodiments, the receptor ligand is platelet-activating factor. In preferred embodiments, the receptor ligand is implicated in such inflammatory disease syndromes as hyperacute organ transplant rejection, iscemic bowel necrosis, or adult respiratory distress syndrome.

In other embodiments of the invention, the receptor ligand binds to a cell surface receptor which plays a role in the development of a cancer. For example, in some embodiments the receptor ligand binds to a cell surface receptor that facilitates infection by a known or suspected human tumor virus, preferably an Epstein-Barr virus, a T-cell leukemia virus, a Hepatitis B virus or a high-risk Papilloma virus. Appropriate receptor ligands for use in treating an Epstein-Barr infection, and thus preventing potential downstream oncogenic transformation events, are discussed further below. Preferred receptor ligands for treating human T-cell leukemia virus (HTLV-1) are those which bind to the T-cell and neuron-specific receptors infiltrated by this virus, while an Hepatitis B virus infection, which can lead to primary hepatocellular carcinoma, is logically treated with formulations containing agonists of the liver, kidney and pancreas-specific cell receptors utilized by this virus. In some embodiments, the receptor ligand of the invention functions a mediator of cell growth regulation. As mentioned earlier, epidermal growth factor frequently functions as an autocrine stimulator of solid human tumor growth, and so preferred formulations of solid tumor therapeutics would therefore incorporate this receptor ligand. Thus in general, in many human cancers known to involve paracrine or autocrine signaling by growth factors, the receptor ligand of choice in formulating the therapeutic agonist composition is the growth factor or transforming growth factor implicated in this process. For example, as discussed in more detailed in the background, the receptor ligands interleukin 1 and tumor necrosis factor have been implicated in a number of human cancers, such as human cervical carcinoma and are thus the receptor ligands of choice in treating these forms of cancer. In another example, antagonist complex formulations incorporating a bombesin-like neuropeptide growth factor would be expected to act as effective therapeutics for treating human small cell lung cancers. In still other embodiments, the receptor ligand of choice is an effector of the progression of a benign to a malignant cancer. For example, a suitable receptor ligand for use in treating such later stages in the progression of cancer are effectors of neovascularization, preferably a vascular endothelial growth factor or a basic fibroblast growth factor. The receptor ligand of choice in cancer therapeutic formulations can further be an effector of tumor cell migration, preferably a urokinase plasminogen activator molecule.

In general, pharmaceutical formulations for treating human cancers will incorporate a receptor ligand, frequently a mitogenic growth factor. In most instances, the exact choice of receptor ligand will be informed by the precise form of cancer to be treated or prevented. For example, for individuals at high risk for specific forms of familial inheritance of a specific cancer, the preventive therapeutic will incorporate growth factors or other receptor ligands known to frequently function in the autocrine, paracrine or endocrine induction of the relevant cancer. For treatment of a specific form of cancer, the choice of receptor ligand will rely upon the knowledge in the art regarding that tumor type. Furthermore, therapeutic formulations containing vascular endothelial growth factor or basic fibroblast growth factor or urokinase plasminogen activator are likely to serve as effective therapeutics for treating most forms of human cancer involving the formation of solid tumors and metastatic movement of transformed cells.

Other therapeutic formulations of the present invention are intended for treating human infections. For example, the Epstein-Barr virus is known to utilize the CR2 (C3d) receptor, described above for its involvement in the complement system, and so the receptor ligand of choice in designing a suitable therapeutic would be a known CR2 ligand such as iC3b. In contrast, infection of neurons by rabies virus is mediated by acetylcholine receptors and so acetylcholine or acetylcholine analogs would be receptor ligands of choice in designing anti-rabies therapeutic formulations. In contrast the alpha togaviruses and the flaviviruses are able to bind to receptors expressed on cells of many animal species, including arthropods, reptiles, amphibians, birds, and mammals. This allows them to infect and to be spread by animals, mosquitos, and other insects. Thus, the choice receptor ligand in this instance would be one which binds to this class of species-nonspecific receptor.

Furthermore, in a preferred embodiment of the invention, the infectious agent is the HIV-1 virus and the receptor is a chemokine receptor. Thus, the receptor ligand of choice in this instance would be a known chemokine such as MIP-1α, MIP-1β, RANTES, MDC, I-309, eotaxin, MCP-3, or SDF-1. The preferred ligand for treating an HIV-1 is defined by the coreceptor tropism of the infecting HIV-1 population, which, at least in part, is determined by the stage to which the infection has progressed. For example, macrophage-tropic (M-tropic) strains of HIV-1 replicate in macrophages and $CD4^+$ T cells and use the CC chemokine receptor CCR5. This co-receptor is used by almost all primary HIV-1 isolates regardless of viral genetic subtype, and by the related lentiviruses HIV-2 and simian immunodeficiency virus (SIV). In contrast, T-tropic isolates of HIV-1 replicate in primary $CD4^+$ T cells, established T cell lines, as well as macrophages; and these viruses use the CXC chemokine receptor CXCR4, and, in some instances, CCR5 as well. Those viruses that only use the CXCR4 receptor are referred to as X4 subclass HIV viruses, whereas viruses that use both receptors with comparable efficiency are referred to as R5X4. Nine other chemokine receptors have also been implicated as potential HIV co-receptors. Table 1 summarizes what is currently known about chemokine receptors known or suspected to functions as co-receptors for HIV infection. In particular, the table summarizes the chemokine(s) known to function as receptor ligands for each of these receptors and thus teaches preferred receptor ligands for antagonizing the various HIV-1 subtypes.

TABLE 1

Summary of HIV and SIV co-receptors

| Chemokine Receptor | Ligand Type | Ligand | Virus |
|---|---|---|---|
| CXCR4 | CXC | SDF-1 | X4, R5X4 |
| CCR2 | CC | MCP-1, MCP-2,. MCP-3 | R5X4 |
| CCR3 | CC | Eotaxin, RANTES, MIP-1α, MCP-3, MCP-4 | R5X4 |
| CCR5 | CC | MIP-1α, RANTES, MIP-1β | R5, R5X4, HIB-2, SIV |
| CCR8 | CC | 1–309[46] | R5X4, HIV-2, SIV |
| STRL33/BONZO | ? | ? | R5X4, SIV |
| BOB/GPR-15 | ? | ? | R5X4, SIV |
| GPR-1 | ? | ? | SIV |
| V28/CX,CR | CX,C | Fractalkine | R5X4, HIV-2, SIV |
| APj | ? | ? | R5X4, SIV |
| US28 (cytomegalovirus) | CC | RANTES, MIP-1α, MCP-1 | R5X4 |

The above table provides information valuable for developing specific anti-HIV formulations of this invention. For example, there is evidence that transmission of HIV is mainly restricted to R5 strains of the HIV virus during person-to-person contact (reviewed in Moore and Trkola (1997) AIDS Res. Hum. Retro. 13: 733–6). Furthermore, individuals homozygous for a deletion of the CCR5 receptor are highly resistant to infection with R5 viruses. These findings suggest that candidate anti-HIV therapeutics should focus on the CCR5 co-receptor and thus preferred formulations of the present invention incorporate CCR5 receptor signaling chemokines, such as RANTES, MIP-1a, or MIP-1b. Indeed, all M-tropic strains of HIV-1, regardless of their geographic lade, appear to target the CCR5 co-receptor (Scarlatti et al. (1997) Nature Med. 3: 1259–65), and thus the CCR5 co-receptor antagonists of the invention offer hope as universal inhibitors of HIV infection, regardless of the existence of multiple genetic subtypes found in different infected human populations. In contrast, the more virulent R5X4 and X4 subclass HIV viruses emerge in approximately 50% of patients late in the course and are often associated with a rapid disease course (Schuitemaker et al. (1992) J. Virol. 66:1354–60). These findings suggest that effective anti-HIV therapeutics for use in treating later stage of HIV-1 infection and resulting AIDS, should focus on antagonists of the CXCR4 co-receptor such as SDF-1.

Other formulations of the invention are useful in treating microbial infections by a bacterium or fungus. For example. the initial colonization of a tissue by a pathogenic bacterium often requires the interaction between adhesins present on the bacterial cell surface, and specific glycoprotein or glycolipid receptors on the host cells. For example, group A Streptococcus is thought to adhere to N-acetyl-D-glucosamine cell surface receptors, while *Escherichia coli* infections require host GM ganglioside receptors and P blood group glycolipid receptors. Furthermore, *Treponema pallidum* targets fibronectin receptor while Chlamydia species utilize N-acetyl-D-glucosamine cell receptors. Thus preferred formulations of the present invention for treating these microbial infection would utilize receptor ligand molecules targeted to each of these microbial targets for bacterial adhesin interaction. In some embodiments, the formulation incorporates the bacterial adhesin itself. For example, *Staphylococcus aureus* utilizes a lipoteichoic acid adhesin and so anti-Staph. formulations of the invention would incorporate lipoteichoic acid, or derivatives thereof, as the preferred receptor ligand. Similar logic could be applied to group A Streptococcus, which utilizes an LTA-M protein complex as an adhesin, and *Mycoplasma pneuomoniae*, which utilizes a microbial cell surface adhesin known as protein P1. Furthermore, the parasitic fungus *Candida albicans* utilizes a fungal mannan molecule as its adhesin, and so anti-Candida therapeutics would incorporate this molecule as the receptor ligand component.

Still other formulations of the invention are useful to treat microbial toxin-producing infectious agents. For example, many bacterial exotoxins conform to a bipartite structural plan composed of A and B subunits. These toxins bind to cell surfaces through the B subunit, and then the A subunit is transferred into the interior of the cell where cell injury is produced. Thus preferred receptor ligands for use in pharmaceutical formulations of the present invention would incorporate receptor ligands which bind to the B-subunit-targeted cell surface receptor and thereby prevent interaction with the microbial exotoxin. For example, cholera toxin targets the ganglioside ($GM_1$) receptors present on the surface of human intestinal cells, resulting in the activation of adenylate cyclase which leads to secretory diarrhea. Therefore effective anti-cholera toxins would incorporate ligands capable of binding to gangliosides, which are glycolipids which contain N-acetlyneuraminic acid. Similarly the choice of receptor ligand for treating other microbial-toxin-producing infections would depend upon the offending microbe and resulting B-subunit-targeted cell surface receptor. For example, Botulinum toxin likely targets another ganglioside receptor ($GD_{1b}$) and tetanus toxin may also make use of this ganglioside receptor and so ganglioside-binding ligands would again be the preferred receptor ligand component of an anti-botulism and anti-tetanus formulations. In contrast, anthrax toxin, diphtheria toxin, pertussis toxin and shiga toxin appear to target glycoprotein receptor and so preferred receptor ligands for use in treating these toxins would correspond to appropriately-chosen glycoprotein receptor binding molecules.

While the above examples serve to illustrate some of the major therapeutic applications of the receptor ligand-containing antagonist complexes of the invention, many other naturally occurring and synthetic receptor ligands agonists are known to exist and are their use in receptor ligand-containing antagonist formulations is included in the method of the present invention.

In preferred embodiments of the present invention, the receptor ligand molecule is a protein that binds to a glyscosaminoglycan, such as heparin. Many important regulatory proteins bind tightly to heparin, including chemokines, growth factors (including cytokines), enzymes and proteins involved in lipid metabolism. This binding property was, for a long time, thought to arise only from non-specific ionic interactions involving positively charged regions on the proteins with the negatively charged sulfates of heparin. However, recent results with two proteins, Anti-thrombin III (AT III) and basic fibroblast growth factor (bFGF), demonstrate that the interactions between heparin and AT III or BFGF can show specificity. The specific interaction involves complex binding sites an the protein molecule and infrequently occurring sequences in the heparin GAG chain. See, for example, EPO patent publication EP 0,509,517 A2, published Oct. 21, 1992; Turnbull et al., (1992) J. Biol. Chem. 267:10337–10341; Gallagher et al., (1992) Glycobiology 2:523–528; Habuchi et al., (1992) J.Biochem. 285:805–813; Yayon et al., (1991) Cell 64:841–848; and Repreager et al., (1991) Science 252:1705–1708.

Other examples of heparin-binding receptor ligands include, for example, the chemokines. The chemokines represent a family of cell signaling factors which have closely related structures and certain common functional features, including the ability to bind heparin. At least 15 member molecules have been identified to date. Among the better characterized chemokines are Platelet factor 4 (PF4) and Interleukin 8 (IL8). PF4 was originally identified on the basis of its ability to bind to heparin. While the structural characteristics of this protein are well characterized, its physiological role remains obscure. It is known that PF4 can neutralize heparin's anticoagulant activity by binding to heparin. Because other chemokines also can interact with heparin, it is possible but not proven, that other members of the chemokine family can also neutralize heparin. It has been suggested that PF4 may provide a natural regulatory effect for coagulation by binding to heparan sulfate on the endothelial cell surface but, to date, such binding has not been directly demonstrated in vivo.

Although PF4 does not have significant demonstrable effects on leukocytes many of the other chemokines appear to be intimately involved in the trafficking of these cells. It has been proposed that these factors play an important role in the normal maintenance of the immune system and participate in a number of pathological conditions, such as inflammatory disturbances, autoimmune disorders, sepsis and atherogenesis. See, for example, Oppenheim, et al. (1991) *Annu. Rev. Immunol.* 9:617–648. Consistent with this concept, the chemokines have been shown to be somewhat selective attractants and activating factors for various subtypes of leukocytes. For example, IL-8 is a potent attractant and activator for neutrophils and possibly a certain lymphocyte subset but has no detectable activity on monocytes. By contrast, MCP-1 is a potent chemoattractant for monocytes but displays no known activity on neutrophils. Other members of the family have partially specific but often overlapping activities and presently it is not clear how specific signaling of these proximal leukocyte mediators may be mediated. As chemokines are direct simulators of critical subtypes of immune and/or inflammatory cells, they represent important targets for the development of pharmacological compounds which specifically inhibit or modify the action of chemokines.

From a functional standpoint, the best characterized chemokine is IL-8. Based on the conserved structural and functional features of members of the chemokine family, it is expected that the mechanism of IL-8 action will serve as a model for other members of the chemokine family which are produced in the parenchyma, either by parenchymal cells or by leukocytes that have extravasated to sites within the tissue. While IL-8 can be produced by a variety of cell types within the parenchyma, it also can be produced by certain activated leukocytes. In vivo, production of chemokines in leukocytes is likely to be a secondary event, occurring after the leukocytes have entered sites of inflammation and have become activated.

The expression of IL-8 and the means by which it acts to attract neutrophils has been studied both in vitro and in vivo. Endothelial cells in culture are reported to produce and localize IL-8 when stimulated with pro-inflammatory factors. Moreover, studies involving skin tissue show that exogenously added IL-8 can preferentially associate with certain regions within the microvascular endothelium. It also has been proposed, based on in vitro data, that neutrophils preferentially traverse a gradient of IL-8 associated with the substrate (i.e. a haptotactic gradient rather than chemotactic gradient). Accordingly, it is possible that part of the chemokine mechanism of action is by means of localization to a cell surface and creating a gradient across which activated leukocytes can migrate.

Finally, another member of the chemokine family MIP-1β, has been shown to bind to both heparin-BSA conjugates and a leukocyte derived proteoglycan, CD44. Binding to these molecules under the experimental conditions employed led to an enhancement of the ability of MIP 1β to activate lymphocytes. It is possible, therefore, that the functional form of MIP1β in vivo is bound to proteoglycans, although the actual molecule or molecules for specific attachment remain unknown. MIP1β also has been shown to be associated with endothelial cells within the lymph nodes in vivo, possibly by means of a cell surface proteoglycan.

While IL-8 has been well established as a simulator of neutrophils, it also has been reported to have anti-inflammatory action. In the reports, however, IL-8 was injected directly into the bloodstream, producing a concentration gradient inverse to that occurring under physiological conditions, and one likely to have significant adverse consequences in therapeutic applications. It would be desirable to improve upon this with a specific antagonist of the action of individual chemokines.

It is well recognized that the endogenous heterooligodisaccharides heparan sulfate and heparin bind with appreciable affinity to a wide spectrum of the mitogenic proteins termed cytokines and growth factors, although the strength of these interactions varies considerably among the different factors. Among the growth factors and cytokines described as heparin/HS-binding proteins are: TGF-P, endothelial cell growth factor, IL3 and GM-CSF, interferon-γ, hepatocyte growth factor, fibroblast growth factor (FGF) family [FGF-I (acidic FGF), FGF-2 (basic FGF), FGF-3 (int-2), FGF-4 (Hst-'L, K-FGF), FGF-5, FGF-6. (Hs-L.-2) and FGF-7 (keratinocyte GF). For example, heparin will release TGF-β from inactive complexes with a 2_macroglobulin and will potentiate TGF-β action. The stability in solution of acidic and basic FGF (AFGF and bFGF) is enhanced in the presence of HS/heparin, and the polysaccharides potentiate the mitogenic activity of the FGFs, especially of AFGF. These effects are presumed to be due to the formation of complexes between FGF and heparin which prolong the biological lifetime of the proteins by protecting them from proteolysis and thermal denaturation. In tissues, AFGF and BFGF can be detected in the extracellular matrix and basement membranes, where they are bound to HS. It has been proposed that the action of heparinases or proteases that degrade heparan sulfate proteoglycans will release FGFs from the basement membranes enabling them to act on nearby target cells. In addition to effects on FGF stability and tissue localization, a central role has now been described for HS in controlling the interaction of BFGF with cell signaling receptors.

Several important proteins of lipid metabolism are known to bind heparin and to be regulated by this interaction. One example is lipoprotein lipase, an extracellular enzyme which is able to initiate and facilitate the process of cellular uptake of blood, lipids in several ways (Olivecrona, T. and Bengtsson-olivecrona, G. (1987), Lipoprotein Lipase, (Borenszajn, J. ed.) pp. 15–58 Evener Publishers Inc., Chicago). The activity of this enzyme appears to be regulated by binding to heparan sulfate on the cell surface and in the extracellular matrix (Williams et al., (1992) J. Biol. Chem. 267: 13284). Current thinking holds that this binding interaction is quite non-specific in nature as it may be competed by the addition of either heparan sulfate or dermatin sulfate which are structurally distinct polyanionic polysaccharides (Saxena et al. (1992) J. Biol. Chem. 268: 14812). Other proteins involved in lipid metabolism such as, for example, two subunit proteins of blood lipid transport complexes, apolipoprotein B and apolipoprotein E, also are known to bind to heparin and heparan sulfate and cellular uptake may be regulated by this interaction (Ji et al. (1993) J. Biol. Chem. 268: 10160). This binding also is suggested to depend an non-specific, ionic interactions (Radhakrishnamurthy et al. (1990) Eur. Heart J. 11 Suppl. E, 148). Finally, high affinity binding of LDL to its receptor, which is required for internalization of the complex, may be facilitated by initial interaction with cell surface heparan sulfate.

Amyloid diseases are caused, in part, by the self-association of amyloid protein—to form insoluble fibrillar complexes within and around cells thereby impeding normal cellular function. Recent studies have shown that glycosaminoglycans, likely associated with the extracellular matrix, especially heparan sulfate (Buee et al. (1993) Brain Res. 601: 154) and chondroitin sulfate (DeWitt et al. (1993 Exp-Neurol. 121: 149), colocalize in these amyloid aggregates and it has been suggested that glycosaminoglycans participate directly in the formation of amyloid fibril formation (de Beer et al. (1993) J. Biol. Chem. 268: 20606). Drugs which are able to selectively block the association of amyloid proteins may be expected to provide prophylactic and/or therapeutic benefit in a variety of amyloidoses, for example, Alzheimers Disease, inflammatory amyloidoses, and prior diseases.

Selectins are leukocyte adhesion molecules involved in the first step of leukocyte extravasation. Three selectins are known to exist, L-selectin (leukocyte), P-selectin (platelet), and E-selectin (endothelial cell). L-selectin appears to be exclusively found on leukocytes, while both E and P selectin are found on endothelium and elsewhere. The molecules or counter-receptors on the surface of a neighboring cell which are specifically bound by selectins during the process of adhesion have not been fully characterized although selectins have been shown to bind to oli-gosaccharide structures, especially sialyl Lewis X (Polley et al. (1991) Proc. Nat. Acad. SCi., USA_88: 6224). More recently, binding to sulfated sugars, including GAG structures has been reported (Lasky et al. (1992) Cell 69: 927, Fiezi, T. et al. (1993) J. Cell Biochem- Supp, 17A:372, and Norgard et al. (1993) FASEB Journal 7: A1262). Selectins appear to be an example of an effector protein in which the binding of the glyceptor is the primary effector function of the molecule.

Serum soluble glyceptor analogs which are specific for one or more selectins may be expected to prevent the first step of leukocyte adhesion, thereby abrogating an inflammatory or immune response.

Examples of other naturally-occurring receptor ligands which are widely known in the art include effectors of endocrine, paracrine or autocrine signaling events. Such effectors include, for example, hormones, pheromones, neurotransmitters, and growth factors. The receptor ligand of the present invention may be a member of any of a number of chemical classes of compounds known or suspected of acting as extracellular signaling agents. Such chemical classes of receptor ligands of the present inventions include amino acid derived receptor binding molecules such as epinephrine, norepinephrine, and histamine or derivatives of arachidonic acid such as the prostaglandins. In preferred embodiments of the present invention, the receptor ligand is a peptide growth factor such as glucagon, insulin, gastrin, secretin, cholecystokinin, adrenocorticotropic hormone (ACTH), follicle stimulating hormone (FSH), leutenizing hormone (LH), thyroid-stimulating hormone (TSH), parathyroid hormone, vasopressin, TSH-releasing hormone (TRH), or LH-releasing hormone (LHRH). In still more preferred embodiments of the present invention, the receptor ligand is a peptide growth factor or a differentiation factor such as epidermal growth factor (EGF), somatotropin (growth hormone), erythropoieting, granuloctye-macrophage colony-stimulating factor (GM-CSF), interleukin 1 (IL-1), interleukin 2 (IL-2), nerve growth factor, or insulin-like growth factor 1 (IGF-1 or somatomedin 1). In preferred embodiments of the present invention, the receptor ligand is a water-soluble molecule which interacts with a cell-surface receptor.

In other embodiments of the invention, the receptor ligand is a synthetic compound known or suspected of acting on a cell surface receptor. Such synthetic compounds are widely known in the art and are exemplified in part by the wide range of pharmacologically active drugs which are known or suspected of binding to cell surface receptors. Such drugs may act as receptor agonists, in which case the present invention provides for a means of converting them into receptor antagonist complexes. Alternatively, where pharmacologically active receptor ligands are not available to antagonize the function of a specific receptor, suitable synthetic receptor ligand binding molecules can readily be identified by virtue of their affinity for a known receptor. Assays available to facilitate identification of such compounds include many protein-protein and protein-carbohydrate interaction assays known in the art and enumerated below.

Preferred receptor ligands of the present invention are small, biologically active polypetides that bind to glycosaminoglycans such as heparin and heparan sulfate. Such heparin-binding polypeptides include cytokines (also termed chemokines) such as platelet factor 4 and IL-8 (Barber et al. (1972) Biochim. Biophys. Acta 286: 312–29). Heparin-binding growth factors have been defined biochemically as a group and include many members (Burgess and Maciag (1989) Annu. Rev. Biochem. 58: 576–606; Klagsbum, et al. (1989) Prog. Growth Factor Res. 1:207–35). They include epidermal growth factor (EGF), platelet-derived growth factor (PDGF), basic fibroblast growth factor (bFGF), acidic fibroblast growth factor (aFGF), vascular endothelial growth factor (VEGF), and hepatocyte growth factor (HGF) and selecting, such as L-selectin, E-selectin and P-selectin (Norgard-Sumnicht et al. (1993) Science 261:480–3).

As mentioned earlier, the present invention derives, at least in part, from the observation that chemokine-glycosaminoglycan complexes retain the ability of the chemokine to suppress HIV-1 infection, but do not trigger normal receptor signaling. Based on the similar extracellular recognition of a receptor by infectious agents other than HIV and the involvement of receptor-ligand mediated signaling pathways in many diseases and conditions, the invention thus features a variety of novel receptor ligand containing antagonists and their use in preventing and treating certain diseases as have been enumerated above. Following the selection of a suitable receptor ligand following the guidelines set out above, the designer of the rational antagonist complex of the present invention has only to select a suitable receptor ligand binding molecule and a method for formulating complexes between this receptor ligand binding molecule and the appropriately selected receptor ligand. The various suitable embodiments of such receptor ligand binding molecules are enumerated below.

4.3.1.2 Receptor Ligand Binding Molecules

The receptor ligand binding molecule as described above, can be a natural or a synthetic molecule that binds the ligand with some affinity, but it is generally not the cell receptor which is targeted by the receptor ligand component of the invention. Indeed the selection of, for example, the extracellular domain of a targeted cell surface receptor, or a fragment thereof, would, be inappropriate to serve as the receptor ligand binding molecule, since it would inevitably act to compete away binding by the receptor ligand and prevent the formation of a receptor/ receptor ligand/ receptor ligand binding molecule ternary complex, which is a preferred mode of action of the therapeutic receptor ligand antagonist complexes of the present invention.

As the present invention is partly based upon the surprising observations concerning anti-HIV chemokine/ glycosaminoglycan formulations, preferred embodiments of the receptor ligand binding molecule are glycosaminoglycans. It is worth noting here that glycosaminoglycans such as heparin have been reported to act as anti-HIV-1 infectious compounds in cell culture experiments (see Lederman, S. et al (1989) J. Immunol. 143:1149–1154; Baba, M. et al. (1990) J. A.I.D.S. 3:493–499; Harrop, H. et al. (1998) Glycobiology 8:131–137; Rider, Christopher, C. (1997) Glyconj. J. 14:639–642; Rider, Christopher, C. et al. (1994) Biochem. 33:6974–6980; Baba, M. et al., Ann. NY Acad. Sci. 419–421; Coombe, D. R. et al., (1995) Aids Res. Hum. Retrov., 11:1393–1396; Yamamoto, N. et al., Arch. AIDS Res. 1:45–56; Taylor, D. L. et al. (1995) Antivir. Res. 28:159–173; Swart, P. J. et al. (1997) AIDS Res. Hum. Retrov. 13:677–683; Kuipers, M. E. et al. (1996) J. A.I.D.S. Hum. Retrov. 11:419–429; Patel, M. et al. (1993) A.I.D.S. Res. Hum. Retrov. 9:167–174; and also PCT WO 90/03791). These reports describe the use of high concentrations of heparin which bind to HIV-1 gp120 and inhibit viral attachment to the CD4 receptor. The present invention is distinct from this putative anti-HIV therapeutic in that it operates, in preferred embodiments, as a formulation with a receptor ligand molecule. Furthermore the resulting receptor ligand/ receptor ligand binding molecule formulation is capable of forming an anti-HIV ternary complex with the targeted chemokine receptor which prevents receptor mediated HIV-1 infection.

Preferred examples of appropriate receptor ligand binding molecules of the present invention include polyanionic compounds, such as glycosaminoglycan. Preferred glycosaminoglycans are heparin, heparin sulfate, chondroitin sulfate, or dermatan sulfate.

Glycosaminoglycans (also referred to herein and in the art as "glycans") can be divided into four main classes on the basis of the repeating disaccharide unit in the backbone. Typically, one sugar is a uronic acid, and the other is either an N-acetylglucasamine or an N-acetylgalactosamine. The classes are exemplified by the following four GAGS: (1) heparan sulfate (Dglucuronic acid/N-acetyl- or N-sulfo-D-glucosamine); (2) chondroitin/dermatan sulfate (D-glucuronic acid or L-iduronic acid/N-acetyl-D-glactosamine); (3) keratan sulfate (D-galactose/N-acetyl-D-glucosamine), and (4) hyaluronic acid. All GAG'S, with the exception of hyaluronic acid, contain sulfate groups variously esterified to the ring hydroxyl groups of the sugars. These negatively charged groups are believed to figure prominently in the biological properties attributed to glycosaminoglycans. The naturally-occurring forms of GAC's, particularly heparin, heparan sulfate, chondroitin sulfate and dermatan sulfate, in fact are complex hetero-oligosaccharides composed of mixtures of differentially sulfated sugar residues.

One of the most thoroughly studied glycosaminoglycans is the widely used anticoagulant heparin. Heparin is a highly sulfated form of heparan sulfate, which is found in most cells. As a commercial product, heparin is a hetero-oligosaccharides composition of about 20–60 monomeric units, having an overall extended length of about 100–300 A, having no protein associated with it, and its anticoagulant properties can be ascribed exclusively to the specific sulfation patterns found on the carbohydrate chains. So-called "low molecular weight" heparin typically is a hetero-oligosaccharides composition of about 25–30 monomeric units, having an overall extended length of about 40A. Heparin is known to have a variety of potentially useful biological activities beyond its ability to inhibit blood coagulation including, for example. the ability to block complement activation, smooth muscle cell proliferation and tumor growth. However, the toxicity of heparin at the levels required to manifest these activities in vivo has limited its clinical use. Heparan sulfate, the predominant GAG on cell surfaces, contains fewer sulfate groups than heparin and has been shown to contain regions of high sulfation interspersed among regions of low or no sulfation.

Other polysulfonated compounds described in the art and asserted to have clinically useful activities analogous to those attributed to heparin include fractions or fragments of the naturally-occurring GAG's, pentosan polysulfate (PPS), dextran sulfate, chondroitin sulfate, and keratan sulfate; and suramin, a polysulfonated napthylurea whose structural motif likely mimics that of a GAG sequence. As for heparin, the toxicity of these compounds at the levels required for therapeutic utility has limited their clinical use. A representative listing of publications describing these compounds and their asserted biological activities includes: U.S. Pat. No. 5,158,940 issued Oct. 27, 1992; U.S. Pat. No. 4,826,827, issued May 2, 1989; international patent publication Nos. WO 90/15816 (public Dec. 27,1990), WO 91/13624 (public Sep. 19,1991), and WO 93/07864 (public Apr. 29, 1993); Wellstein et al. (1991) J. Natl. Cancer Inst. 83:716–720; and Jentsch et al. (1987) J. Gen. Virol. 68:2183–2192.

That specific protein binding sequences might exist in the carbohydrate chain of heparin was first suggested by the observation that some preparations were more effective than others in inhibiting coagulation. Careful studies in 1987 revealed that there is a defined five sugar sequence (pentasaccharide) with a characteristic sulfation pattern that represents the specific binding site for AT III, a protease inhibitor that blocks the action of thrombin and other enzymes which initiate blood coagulation. The Kd for the binding between AT III and this specific GAG recognition site is about 10 (10-am), which qualifies it as a high affinity interaction. Although weaker and less specific binding of these proteins to other regions of heparin can occur, virtually all of the anticoagulant activity of heparin is attributable to this five sugar sequence. This pentasaccharide, generally known as the AT III binding site, now has been synthesized chemically and shown to possess the appropriate activities of the naturally occurring sequence. Binding of antithrombin III to this site is thought to provide the basis for heparin's anticoagulant activity by positioning and "presenting" the enzyme inhibitor to the proteases thrombin and Factor Xa.

A second example of a somewhat specific binding site has been reported for basic fibroblast growth factor. This GAG sequence, isolated from fibroblast heparan sulfate, was found to represent the tightest binding fraction present. It is not clear, however, whether other molecules such as other heparin binding growth factors can bind to this sequence, nor is it clear that the affinity of this binding is as high as the binding between BFGF and heparin. The interaction between the isolated GAG sequence and BFGF might, at present, best be described then as selective, rather than absolutely specific.

It has not been previously demonstrated or predicted that the interaction between the vast majority of glycan-binding proteins and surface-immobilized GAG chains can show any degree of specificity. The unanticipated discovery of such specificity now enables the development of a kind of inhibitory molecule, not previously envisioned, that can specifically antagonize the action of a given glycan-binding protein (see, for example, PCT WO 94/20512). For example, one now can specifically antagonize the action of a given chemokine or growth factor without affecting significantly the action of the remaining members of the protein family. This allows for the design of, for example, of potent and specific anti-HIV chemokine coreceptor antagonists. Moreover, the discovery now enables the development of analogs of specific glycosaminoglycan sequences that can act as agonists or have other utilities in vivo including, for example, as imaging or other tissue-targeting agents.

Methods have been described for identifying and isolating analogs of a glycan sequence having specificity for a given glycan-binding protein (see, for example, PCT WO 94/20512). These methods thus provide means for example, of: antagonizing specific aspects or components of undesirable inflammatory or immune responses, as discussed above, without inhibiting or otherwise adversely affecting beneficial aspects or components of the response; and controlling undesired cell growth and proliferation, as discussed above by combining appropriately formulated glycans with autocrine and paracrine signaling factors which contribute to cancer. Another object of the invention is to provide means for therapeutic and prophylactic manipulation of chemokine, cytokine, enzyme, growth factor and related biological molecule function, including providing novel compositions, and providing a process for discovering useful novel compositions. Such compositions have utility for altering pathologic responses by inhibiting or enhancing the action of one or more members of any of the group of proteins set forth above. The useful compositions contemplated by the invention also include novel tissue targeting agents having general utility.

4.3.1.3. Methods of formulating suitable receptor ligand/receptor ligand binding molecule complexes The present invention includes methods of measuring intermolecular binding interactions for the purpose of designing, selecting or screening appropriate therapeutic formulations. In particular, as discussed above, the design of an effective therapeutic formulation involves the selection of: an appropriate receptor ligand, an appropriate receptor ligand binding molecule, and a method of combining the two. In many instances, such as that discussed above for preferred chemokine/glycosaminoglycan anti-HIV and anti-inflammatory formulations, the choice of a receptor ligand is guided by the receptor (in this instance the chemokine receptor) and the existence of apparent accessory cell surface receptors (in this instance proteoglycan receptors, which consist of an integral membrane core protein to which are attached one or more glycosaminoglycan polysaccharides). In this instance, the known biology of the receptor signaling system serves to guide the informed design of an appropriate receptor ligand (i.e. a chemokine, a known chemokine receptor ligand) and an appropriate receptor ligand binding molecule (i.e. a glycosaminoglycan, a probable chemokine accessory receptor-like molecule). Furthermore, as described in the exemplification supporting the formulation of an anti-HIV therapeutic, where any of a number of incubation times and temperatures were adequate to generate HIV-suppressive complexes, the method of combining the two components is trivial in the instance where the receptor ligand has a natural affinity for the receptor ligand binding molecule.

Numerous analogous situations exist in which a receptor to be targeted is known, and this knowledge informs both the choice of the receptor ligand and a suitable receptor ligand binding molecule. For example, as was previously described, human cancers are frequently found to be responding to autocrine mitogenic signaling events. In particular, several members of the fibroblast growth factor family have been implicated in these autocrine oncogenic processes. For example, the high-level expression and secretion of fibroblast growth factor-2 (FGF-2 or bFGF) is frequently found in adult tumors (Slavin (1995) Cell Biol. Internat. 19: 431–44). In one study, immunohistochemical analysis indicated the presence of secreted FGF-2 in the extracellular matrix of most adult gastrointestinal tumor specimens. Thus, much as discussed earlier in the section on receptor ligands of the present invention, a therapeutic effective in the treatment of adult solid gastrointestinal tumors might logically incorporate the FGF-2 growth factor into a suitable receptor ligand antagonist complex. An appropriate receptor ligand binding molecule is, in this instance, suggested by the biology of the fibroblast growth factors and their receptors. Indeed high affinity binding and signaling by FGF-2 is thought to involve interactions of FGF-2 with both its receptor (fibroblast growth factor receptor-1 or FGFR-1) and a cell surface heparan sulfate proteoglycan receptor. Indeed, mutations in the heparin binding domain of various fibroblast growth factors have been shown to block FGF-dependent signaling events. Furthermore the fibroblast growth factors are known in the art to bind and form complexes with free heparin (see, for example, U.S. Pat. No. 5,464,815). Therefore, in this situation, free heparin is a preferred form of the receptor ligand binding molecule both because of its likely ability to prevent interaction with an obligate coreceptor utilized by the receptor ligand, and because of its natural avidity for the ligand of choice.

In certain other applications of the method of the invention, the choice of the receptor ligand and receptor ligand binding molecule may require additional analysis. In still others, the method of combining the two components into a formulation may require additional analysis or manipulation of the components.

4.3.2 Effective Dose

Toxicity and therapeutic efficacy of such compounds can be determined by standard pharmaceutical procedures in cell cultures or experimental animals, e.g., for determining The LD50 (The Dose Lethal To 50% Of The Population) And The $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.3.3 Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The pharmaceutical formulation of the present invention may also be formulated in vaginal or rectal compositions such as suppositories or retention enemas, e.g., containing conventional suppository bases such as cocoa butter or other glycerides. Particularly useful for prevention of HIV infection/transmission resulting from sexual intercourse are various foam or gel based compositions including those which additionally incorporate a contraceptive agent. The pharmaceutical formulation may be conveniently presented in discrete dosage units and may be prepared by any of the methods well known in the art of pharmacy. Formulations suitable for vaginal administration may be presented as pessaries, creams, gels, pastes, jelly, foams or sprays or aqueous or oily suspensions, solutions or emulsions (liquid formulations), or films containing, in addition to the receptor ligand/receptor ligand binding molecule (e.g. chemokine/glycosaminoglycan) formulation, such carriers and stabilizing agents as are known in the art to be appropriate.

Appropriate ointments, pastes, jellies, liquids, foams, gels and creams may, for example, be formulated with an aqueous or oil base with the addition of suitable thickening and/or gelling agents. Lotions may be formulated with an aqueous base or an oil base and will in general also contain one or more emulsifying agents, coloring agents, stabilizing agents, suspending agents, thickening agents or surfactants, such as a nonionic surfactant, for example, a polyoxyethylene higher alcohol ether or polyethylene glycol. A gel preparation having a high viscosity can be prepared by adding a conventional thickening agent into the above described liquid preparation. Non-limiting examples of thickening agents include cellulose lower alcohol ether, polyvinyl alcohol (PVA), polyvinylpyrrolidone (PVP) and polyoxyethylene oxypropylene glycol block copolymer. The pH value of the transvaginal or transrectal formulation for use in the present invention should be close to that of the vagina or rectum, i.e. pH 3 to 7, preferably pH 4 to 6. The pH may be adjusted by a non-toxic non-irritating weak acid, such as acetic acid or citric acid, or weak base, such as sodium bicarbonate.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possibiity of local noninvasive delivery of drugs over an extended period of time. This technology utilizes microspheres of precapillary size which can be injected via a coronary chatheter into any selected part of the e.g. heart or other organs without causing inflammation or ischemia. The administered therapeutic is slowly released from these microspheres and taken up by surrounding tissue cells (e.g. endothelial cells).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

In clinical settings, a gene delivery system for the therapeutic receptor antagonist can be introduced into a patient by any of a number of methods, each of which is familiar in the art. For instance, a pharmaceutical preparation of a gene delivery system can be introduced systemically, e.g., by intravenous injection, and specific-transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, a gene delivery vehicle can be introduced by catheter (see U.S. Pat. No. 5,328,470) or by stereotactic injection (e.g., Chen et al. (1994) PNAS 91: 3054–3057). A receptor antagonist therapeutic, such as any of those discussed can be delivered in a gene therapy construct by electroporation using techniques described, for example, by Dev et al. ((1994) Cancer Treat Rev 20:105–115).

The pharmaceutical preparation of the gene therapy construct or compound of the inventioncan consist essentially of the gene delivery system in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4.4 Methods of Treatment

The receptor ligand-containing antagonist complexes may be administered to treat and or prevent the development of diseases or conditions caused by, or contributed by, the function of a cell surface receptor. Examples of such diseases and conditions include, without limitation: inflammatory diseases, e.g. septic shock, multiple organ failure, hyperacute graft or organ transplant rejection, ischemic bowel necrosis, adult respiratory distress syndrome and complement-mediated inflammatory tissue damage as well as autoimmune diseases including those resulting from or associated with the aforementioned inflammatory diseases and conditions including systemic lupus erythematosus, immune complex glomerulonephritis, and systemic vasculitis; cancer e.g., cancers due to a virus such as a tumor virus including the viruses Epstein-Barr virus, human T-cell leukemia virus (HTLV), Hepatitis B virus, and Papilloma virus, and cancers due directly or indirectly to infection by an HIV virus including HIV-1 including Kaposi's sarcoma, cancers involving the autocrine or paracrine function of a growth factor such as a fibroblast growth factor or an epidermal growth factor or a neuropeptide growth factor or interleukin 1 (IL-1) or tumor necrosis factor (TNF), also cancer involving the growth of steroid hormone-responsive tumors (e.g. breast, prostate, or testicular cancer); vascular diseases or disorders (e.g. thrombotic stroke, ischemic stroke, as well as peripheral vascular disease resulting from atherosclerotic and thrombotic processes); cardiac disorders (e.g., myocardial infarction, congestive heart failure, unstable angina and ishemic heart disease); cardiovascular system diseases and disorders (e.g. those resulting from hypertension, hypotension, cardiomyocyte hypertrophy and congestive heart failure) wound healing; limb regeneration; periodontal regeneration; aid in the acceptance of tissue transplants or bone grafts; skin aging; hair loss; muscle wasting conditions (e.g. cachexia); neurological damage or diseases or neurological or emotional conditions including Alzheimer's disease, Parkinson's disease, AIDS-related complex, cerebral palsy, or depression or neuroendocrine disorders such as hyperthyroidism or hypertension; other diseases conditions or disorders which result from aberrations or alterations of cell receptor-dependent processes including: collateral growth and remodeling of cardiac blood vessels, angiogenesis, cellular transformation through autocrine or paracrine mechanisms, chemotactic stimulation of cells (e.g. endothelial), neurite outgrowth of neuronal precursor cell types (e.g. PC12 phaeochromoctoma), maintenance of neural physiology of mature neurons, proliferation of embryonic mesenchyme and limb-bud precursor tissue, mesoderm induction and other developmental processes, stimulation of collagenase and plasminogen activator secretion, tumor vascularization, as well as tumor invasion and metastasis; or infections due to a virus (e.g. Human Immunodeficiency Virus, an Epstein-Barr Virus, a Rhinovirus, a Poliovirus, a Rabies Virus, a Reovirus, an Influenza Virus, an Herpes Simplex Virus, an Hepatitis virus, a Togavirus, a Varicella-Zoster Virus, a Paramyxovirus, a Cytomegalovirus, a Subacute Sclerosing Panencephalitis Virus, an Adenovirus, a Poxvirus, a Reovirus, a Papovavirus, a Papillomavirus, a Polyomavirus, and a Slow virus), or a microbe, including a bacteria (e.g. *Helicobacter pyloris, Borelia burgdorferi, Legionella pneumophilia, Mycobacterium tuberculosis, Mycobacterium avium, Mycobacterium intracellulare, Mycobacterium kansaii, Mycobacterium gordonae, Mycobacterium leprae, Staphylococcus aureus, Neisseria gonorrhoeae, Neisseria meningitidis, Listeria monocytogenes, Streptococcus pyogenes, Streptococcus agalactiae, Streptococcus faecalis, Streptococcus bovis, Streptococcus anginosus, Streptococcus pneumoniae*, pathogenic Campylobacter species, pathogenic Enterococcus species, *Haemophilus influenzae, Bacillus antracis, Corynebacterium diphtheriae, Erysipelothrix rhusiopathiae, Clostridium perfringers, Clostridium tetani, Enterobacter aerogenes, Klebsiella pneumoniae, Pasturella multocida,* pathogenic *Bacteroides fragilis* group species, *Fusobacterium nucleatum, Streptobacillus moniliformis, Treponema pallidium, Treponema pertenue,* Leptospira, and *Actinomyces isrealli*), a fungus (e.g. *Cryptococcus neoformans, Histoplasma capsulatum, Coccidioides immitis, Blastomyces dermatidis, Chlamydia trachomatis,* and *Candida albicans*); and conditions arising from exposure to a microbial toxin including toxins produce by recognized microbial pathogens (e.g. *Bacillus anthracis,* a pathogenic Bordetella species, *Bordetella pertussis Clostridium botulinum Clostridium tetani, Vibrio cholerae, Corynebacterium diphtheriae, Escherichia coli, Pseudomonas aeruginosa,* and *Shigella dysenteriae*).

The receptor ligand-containing antagonist complexes of the present invention may also be employed to prevent skin aging (e.g., due to sunburn by stimulating keratinocyte growth), or to prevent hair loss, since e.g., family members activate hair-forming cells and promote melanocyte growth. Along the same lines, the polypeptides of the present invention may be employed to stimulate growth and differentiation of hematopoietic cells and bone marrow cells when used in combination with other cytokines.

Various receptor ligands are thought to be important agents in the maintenance of normal cellular and tissue homeostasis. The receptor ligand-containing antagonist complexes of the present invention may therefore also be employed to maintain organs before transplantion or for supporting cell culture of primary tissues.

Furthermore, research on growth and differentiation inducing factors such as the growth factors have shown that they play crucial roles in the repair of damaged tissues and organs and in the regulation of the immune system and can thereby find use in agricultural applications. Specifically, members of this family have been shown to promote skeletal muscle development thereby increasing muscle mass in livestock and obviating the need for excessive use of antibiotics and hormones to improve feed conversion and weight gain in such animals. Transgenic strategies with these factors could lead to new breeds of livestock with significantly enhanced muscle mass and diminished fat content. Furthermore, pharmaceutical applications in humans include use in the development of new therapeutics for intransigent muscle-wasting conditions such as muscular dystrophy and cachexia, the muscle deterioration associated with AIDS and some cancers. The receptor ligand-containing antagonist complexes therapeutics of the present invention may thus have applications in both the improvement of livestock and in the treatment of muscle wasting conditions in humans.

4.5 Screening Assays for Receptor Ligand-Containing Antagonist Therapeutics

The invention further provides screening methods for identifying therapeutically effective formulations of these receptor ligand-containing antagonist complexes for use, e.g., in treating and/or preventing the development of diseases or conditions caused by, or contributed to by, the function of a cell surface receptor.

Cell-free assays can be used to identify compounds which are capable of interacting with a receptor, in order to identify a receptor ligand, or a receptor ligand in order to identify a suitable receptor ligand binding molecule and thereby provide a formulation capable of modifying the activity of a cell receptor and/or the activity of a cell receptor ligand. For convenience, the receptor for which a ligand is to be identified or the receptor ligand for which a receptor ligand binding molecule is to be identified will be referred to here as the binding target. The molecule which binds the binding target will be referred to here simply as the target binding compound. Such a target binding compound can, e.g., modify the structure of a receptor or a receptor ligand and thereby affect its activity. Cell-free assays can also be used to identify compounds which binds a binding target. In a preferred embodiment, cell-free assays for identifying such target binding compounds consist essentially in a reaction mixture containing a binding target and a test compound or a library of test compounds. A test compound can be, e.g., a derivative of a known or suspected receptor ligand or a known or suspected receptor ligand binding molecule.

Accordingly, one exemplary screening assay of the present invention includes the steps of contacting a binding target or functional fragment thereof with a test compound or library of test compounds and detecting the formation of complexes. For detection purposes, the binding target can be labeled with a specific marker and the test compound or library of test compounds labeled with a different marker. Interaction of a test compound with a binding target or fragment thereof can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on multiple sensor surfaces, e.g., which form one wall of a micro-flow cell. A solution containing the binding target or functional fragment thereof is then flown continuously over the sensor surface. A change in the resonance angle as shown on a signal recording, indicates that an interaction has occurred. This technique is further described, e.g., in BlAtechnology Handbook by Pharmacia.

Another exemplary screening assay of the present invention includes the steps of (a) forming a reaction mixture including: (i) a binding target, (ii) a test compound; and (b) detecting interaction of the binding target and the test compound. The binding target and target binding compounds can be produced e.g.

Complex formation between a binding target and a target binding compound may be detected by a variety of techniques. Modulation of the formation of complexes can be quantitated using, for example, detectably labeled proteins such as radiolabeled, fluorescently labeled, or enzymatically labeled binding targets or target binding compounds, by immunoassay, or by chromatographic detection.

Typically, it will be desirable to immobilize either the binding target or target binding compound to facilitate separation of complexes from uncomplexed forms of one or both of the proteins, as well as to accommodate automation of the assay. Binding of a binding target to a target binding compound, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/binding target fusion proteins can be adsorbed onto glutathione sepharose beads (Sigma Chemical, St. Louis, Mo.) or glutathione derivatized microtitre plates, which are then combined with the binding target, e.g. an $^{35}$S-labeled target binding compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of binding target or target binding compound found in the bead fraction quantitated from the gel using standard electrophoretic techniques such as those known widely in the art.

Other techniques for immobilizing proteins on matrices are also available for use in the subject assay. For instance, either the binding target or the target binding compound can be immobilized utilizing conjugation of biotin and streptavidin. For instance, biotinylated binding target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with a binding target can be derivatized to the wells of the plate, and the binding target trapped in the wells by antibody conjugation. As above, preparations of a test compound are incubated in the binding target presenting wells of the plate, and the amount of complex trapped in the well can be quantitated. Exemplary methods for detecting such complexes, in addition to those described above for the GST-immobilized complexes, include immunodetection of complexes using antibodies reactive with the target binding compound, or which are reactive with the binding target and compete with the binding partner; as well as enzyme-linked assays which rely on detecting an enzymatic activity associated with the binding partner, either intrinsic or extrinsic activity. In the instance of the latter, the enzyme can be chemically conjugated or provided as a fusion protein with the target binding compound. To illustrate, the target binding compound can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as anti-binding target antibodies, can be used. Alternatively, the protein to be detected in the complex can be "epitope tagged" in the form of a fusion protein which includes, in addition to the binding target, a second e.g. polypeptide for which antibodies are readily available (e.g. from commercial sources). For instance, the GST fusion proteins described above can also be used for quantification of binding using antibodies against the GST moiety. Other useful epitope tags include myc-epitopes (e.g. see Ellison et al. (1991) J Biol Chem 266:21150–21157) which includes a 10-residue sequence from c-myc, as well as the pFLAG system (International Biotechnologies, Inc.) or the pEZZ-protein A system (Pharmacia, N.J.).

The present invention is further illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning: A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. : 4,683,195; Nucleic Acid Hybridization(B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

5. EXAMPLES

5.1 Cell Culture Methods

PM1 cells were maintained in culture in RPM1-1640 (Gibco BRL) supplemented with 10% BS (Gibco BRL) and 50 µg/ml gentamycin (Sigma). Human PBMC were obtained from healthy donors and collected in EDTA($K_3$) tubes (Vacutainer). Cells were purified by Lymphoprep separation (Beckton Dickinson, San Jose, Calif.). To activate PBMC 5 µg/ml PHA (Sigma Chemical Company, St. Louis, MO) and 20U/ml recombinant human IL-2 (Boehinger Mannheim) were added to the culture for 72 hours. Cells were then washed and cultured in 20U/ml IL-2. Medium was replenished every 2 to 3 days.

5.2 Calcium Mobilization Assays

Activated PBMC were analyzed for $Ca^{+2}$ mobilization as described previously (Burns, et al. (1998) J Exp Med 188: 1917–27; and Bums, et al. (1997) Bio Techniques 23: 1022–26) with the following modifications. Where indicated, PBMC were treated with glycanases to remove cell surface GAG. Cells were incubated with 1 U/ml each of heparinase II, heparinase III, and chondroitinase ABC (Sigma Chemical Company, St. Louis, Mo.) for 1 hour at 37° C. As a control untreated PBMC were simultaneously incubated in RPMI-1640 (Life Technologies, Gaithersburg, Md.) supplemented with 10% fetal bovine serum (FBS) (Life Technologies, Gaithersburg, Md.) and 50 µg/ml gentamycin (Sigma Chemical Company, St. Louis, Mo.), denoted hereafter as complete medium. After 1 hour the cells were washed with complete medium and then RPMI 1640 without phenol red or sodium bicarbonate, but with 25 mM Hepes (Life Technologies, Gaithersburg, Md.). Cells were then loaded with Fluo-3 (Molecular Probes, Eugene, Oreg.) as described (Burns, et al. (1998) J Exp Med 188: 1917–27; and Burns, et al. (1997) BioTechniques 23: 1022–26). RANTES-GAG complexes were analyzed for activity in $Ca^{+2}$ mobilization assays using both enzyme digested and untreated PBMC. The complexes were formed by incubating RANTES (9 µg/ml final concentration) with 1 mg/ml of heparin (Sigma Chemical Company, St. Louis, Mo.), or PBS for 1 hour at 4° C. The formulation was then diluted to bring the concentration of the RANTES component to 3 nM and then analyzed. Data were acquired by a FACSCalibur™ (BDIS, San Jose, Calif.) flow cytometer gating cells by forward and side scatter properties. $Ca_{+2}$ mobilization was determined by analysis in a two-parameter density plot collecting linear emission at 530 nm in the FL-1 window over time.

5.3 RANTES Binding Assays

PBMC were cultured as described above and harvested on Day 8 for the competitive binding assay and Day 10 for the mAb 2D7 blocking assay. Cells were incubated for 1 hr with 1 U/ml each of heparinase II, heparinase III, and chondroitinase ABC (Sigma Chemical Company, St. Louis, Mo.) for 1 hour at 37° C. Cells were washed once in complete medium and once in RPMI 1640 supplemented with 1% bovine serum albumin (BSA). In the blocking assay, cells were incubated with 100 µg/ml of either mAb 2D7 (PharMingen, San Diego, Calif.) (Wu, et al. (1997) J Exp Med 186: 1373–81) or normal mouse polyclonal IgG (Sigma Chemical Company, St. Louis Mo.) in PBS supplemented with 0.1% Na Azide at 4° C. for 1 hour. Cells were then washed once in RPMI 1640 supplemented with 1% BSA and treated with soluble chemokine-GAG complexes. The complexes were prepared by incubating $^{125}$I RANTES (NEN Life Science Products, Boston, Mass.) (0.5 nM) or non-radioactive RANTES (1 µM) with heparin (83 µM) (Sigma Chemical Company, St. Louis, Mo.) for 1 hour at 37° C. prior to addition to cells. Binding assays were performed as described elsewhere (Kuhmann, et al. (1997) J. Virol. 71: 8642–56; and Platt et al. (1 998) 72:2855–64). Briefly, in saturation binding assays serial dilutions of heparin-$^{125}$I RANTES complexes (producing 10 nM to 0.03 nM of the RANTES component) were added to 2×I 06 cells for 1 hour at 37° C. in triplicate reactions. In competitive binding assays, serial dilutions of either mAb 2D7 or unlabeled heparin-RANTES complexes (producing 100 nM to 0.01 nm of the RANTES component) were mixed with iodinated heparin-$^{125}$I RANTES complexes (RANTES component at 0.3 nM) and then added to the cells. The reaction mixtures were then layered over 20% sucrose in PBS and the cells pelleted by centrifugation. Cells were then washed once in PBS supplemented with 1% BSA. Heparin-$^{125}$I RANTES binding was determined by analyzing the cell pellets in a Wallac gamma counter (EG&G Wallac, Gaithersburg, Md.). Background levels of binding were determined by incubating a 300 molar excess of RANTES-GAG with GAG-$^{125}$I RANTES. The total counts added in each assay varied between 30,000 and 227,000. In each case the specific activity was 2200 Ci/mMol.

5.4 HIV-1 Infectivity Assay

Infectivity assays were performed as described previously (Burns, et al. (1998) J Exp med 188: 1917–27) with the following modifications. Activated PBMC were infected for 2 hours at 37° C. with a primary, macrophage tropic HIV-1 isolate, NSI.03 (Connor, et al. (1997) J Exp Med 185: 621–8) at a ratio of 2×10$^6$ cells to 500 TCID$_{50}$ in 5 ml culture medium. Cells were then washed to remove virus and placed in tissue culture wells at a density of 2×10$^5$ cells in 250 µl. Complexes were formed by incubating RANTES (5 µg/ml final concentration) with 1 mg/ml of either heparin, heparan sulfate, chondroitin sulfate or dermatan sulfate for 1 hour at 4° C. to produce complex formulations containing 641 nM chemokine and 83 µM GAG. The resulting complexes were then serially diluted and 250 µl. added to culture wells to achieve a total final assay volume of 500 µl. Control assays were carried out in parallel with sham formulations containing either RANTES or GAG alone at concentrations equal to the amounts present in the RANTES-GAG complex formulations. The cells were fed 3 days post infection by removing 250 µl of medium and replacing with an equal volume of fresh medium containing the appropriate concentrations of RANTES, GAG, or RANTES-GAG complexes. Additional control assays were carried out with medium alone. Levels of infection were determined 6 days post-infection by measuring HIV-1 p24 levels by antigen capture ELISA (duPont).

5.5 Effect of Chemokine-GAG Complexes on Calcium Mobilization

Figure 1:
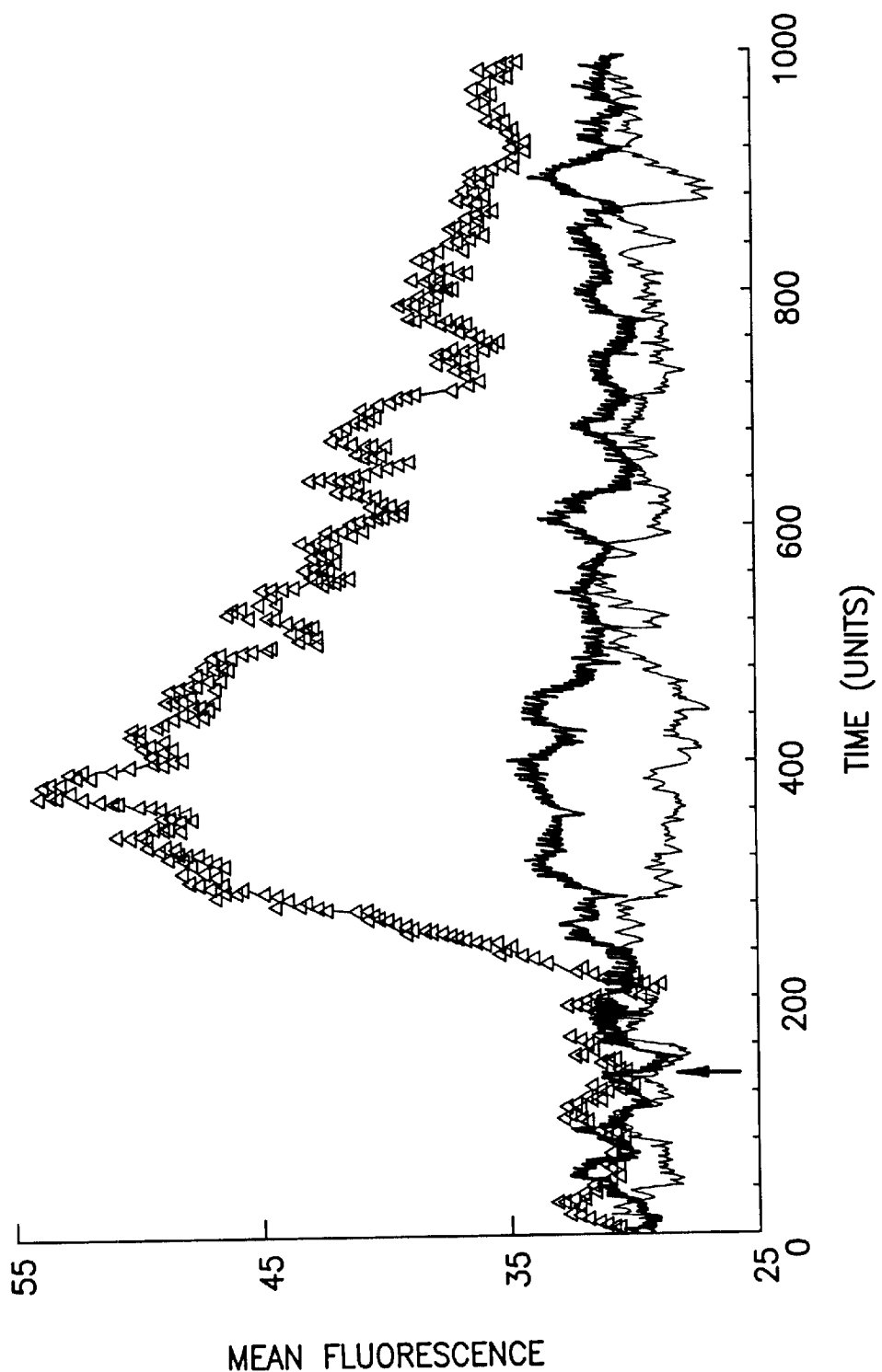
FIG. 1 is a graph showing that glycase treated peripheral blood mononuclear cells (PBMCs) do not mobilize $Ca^{2+}$ in response to RANTES.

In a previous study (Burns et al. (1998) J Exp Med 188: 1917–27) we found that the removal of GAG from cell surfaces by glycanase treatment abrogated the ability of RANTES to stimulate intracellular Ca$^{+2}$ mobilization in PHA-activated PBMC. The ability of RANTES to stimulate intracellular Ca$^{2+}$ mobilization was examined in peripheral blood mononuclear cells (PBMCs) treated with a glycase cocktail of heparinase III, and chondroitinase ABC (FIG. 1). FIG. 1 is a graph showing that glycase treated peripheral blood mononuclear cells (PBMCs) do not mobilize Ca$^{2+}$ in response to RANTES. While intracellular Ca$^{2+}$ mobilization was evident with the untreated PBMCs after exposure to 3nM RANTES, enzymatic treatment eliminated the response (FIG. 1). Similar results were obtained with a number of other chemokines including MIP-1α, MIP-1β, MDC, PARC, TARC, and SDF-1β. Such results are entirely consistent with the concept that GAG are necessary for functional chemokine binding. Normal human PBMCs were activated with PHA and IL-2 for 3 days followed by expansion in the presence of IL-2. On day 15 of culture cells were used to measure the intracellular Ca$^{2+}$ response. Cells were incubated with a glycase cocktail or medium alone and then loaded with the indicator dye Fluo-3, as described in Methods. Untreated (open triangle) and glycase treated (thick line) PBMC were stimulated with 3 nM RANTES and compared to the response of PBS only (thin line) in untreated cells. Fluorescence was measured by flow cytometry in the FL-1 window was collected over time. One time unit is equal to 0.2 sec.

Figure 2:
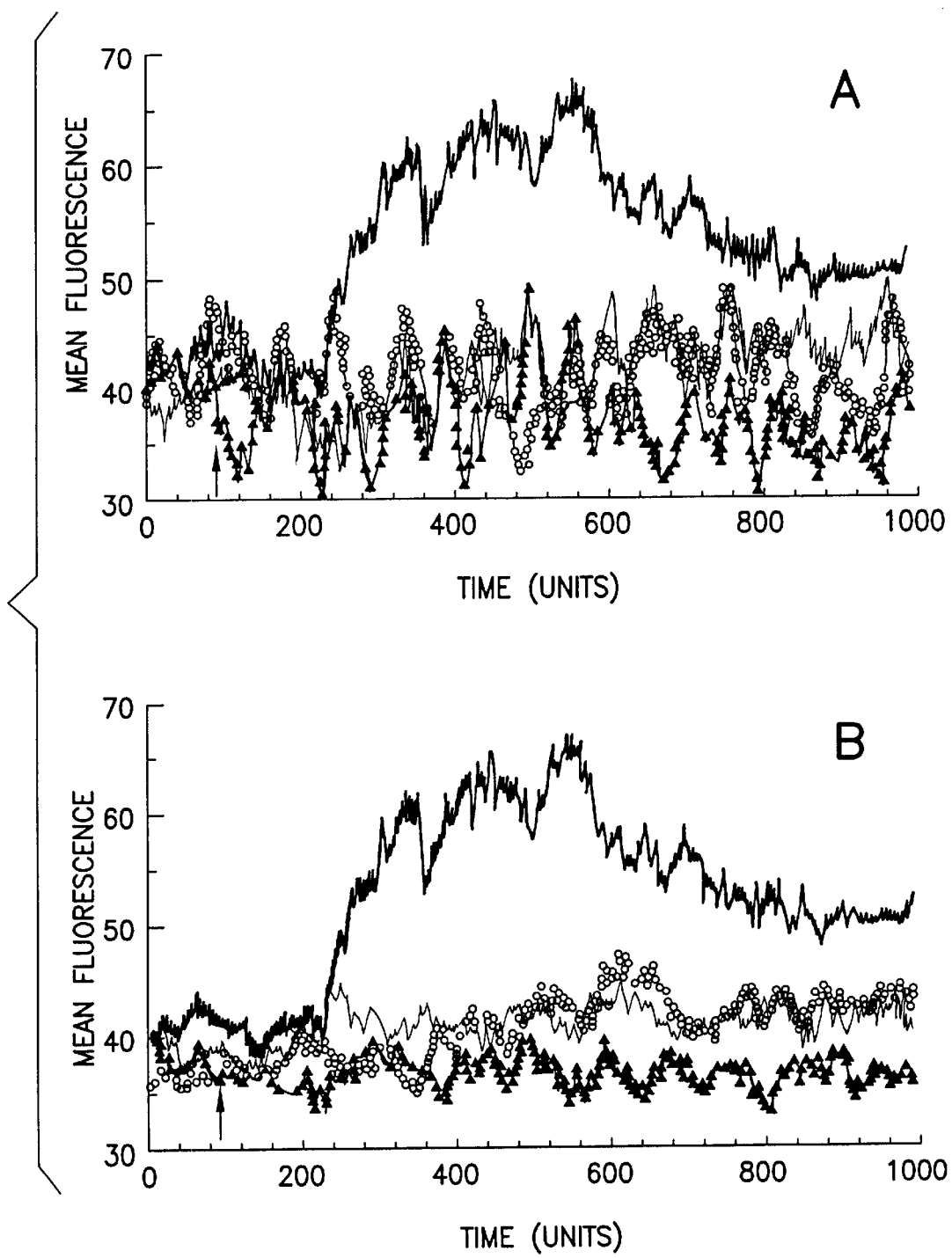
FIG. 2 is a, graph showing that the inhibition of $Ca^{2+}$ signaling in glycase treated (Panel A) and untreated (Panel B) PBMC with RANTES/heparin complex.

To investigate this concept further, restoration of the ability of RANTES to stimulate Ca$^{2+}$ mobilization on glycase treated cells was attempted by incubating the chemokine with heparin in order to form a chemokine-GAG complex. RANTES (94 µg/ml) was incubated with an excess of heparin (1 mg/ml) for 1 hour at 4° C. and tested for the ability to mobilize Ca$^{2+}$ in glycase-treated PBMCs. As shown in FIG. 2, the formation of such complexes failed to compensate for the removal of cell surface GAG and did not stimulate Ca$^{2-}$ mobilization (FIG. 2A). Similarly, complexes formed with RANTES and chondroitin sulfate or dermatin sulfate were also unable to induce a signal (data not shown). Surprisingly, when the experiments were repeated with untreated PBMCs, signaling by RANTES was inhibited by preincubation with either heparin (FIG. 2B), chondroitin a sulfate or dermatan sulfate (data not shown). These results imply that the complexes formed by chemokine binding to soluble GAG are inactive in terms of signaling ability. SDF-1β complexed to the same three GAG produced similar results demonstrating that the phenomenon is not restricted to RANTES (data not shown).

FIG. 2 is a graph showing that the inhibition of Ca$^{2+}$ signal in glycase treated and untreated PBMC with RANTES/heparin complex. Normal human PBMC were activated as previously described and taken on day 11 of culture to measure the intracellular Ca$^{2+}$ response. RANTES (9 µg/ml, final) was incubated with heparin (1 mg/ml) for 1 hour at 4° C. This complex was used to stimulate glycase treated (panel A) and untreated (panel B) PBMC. Glycase treated PBMC (panel A) were stimulated with pre-incubated RANTES/heparin (open circles) heparin alone (open triangles), and PBS (thin line) and these responses are compared to the response induced by RANTES in untreated PBMC (thick line). Untreated PBMC (panel B) were stimulated with pre-incubated RANTES/heparin (open circles), heparin alone (open triangles), PBS (thin line) and RANTES (thick line). Fluorescence was measured by flow cytometry in the FL-1 window was collected over time. One time unit is equal to 0.052 sec. RANTES (1 µM) was incubated with an excess of heparin (83 µM) for 1 hour at 4° C. thus forming complexes of RANTES and GAG. These complexes were then assayed for the ability to stimulate intracellular Ca$^{+2}$ mobilization (Pal et al. (1 997) Science 278: 695–98; Burns et al. (1998) J Exp Med 188: 1917–27; Wu et al. (1997) J Exp Med 186: 1373–81) in peripheral blood mononuclear cells (PBMC) previously treated with heparinase II, heparinase III, and chondroitinase ABC (Sigma Chemical Company, St. Louis, Mo.) as previously described (Burns et al. (1998) J Exp Med 188: 1917–27) to remove surface GAG. Control experiments were also carried out in parallel with untreated PBMC. As shown in FIG. 2A, no increase in intracellular Ca$^{+2}$ was detected in the presence of the soluble RANTES-heparin complexes demonstrating that they could not compensate for the absence of cell surface GAG on the glycanase treated cells. Moreover, the complexes also failed to stimulate Cat$^{+2}$ mobilization in the control assays with untreated PBMC (FIG. 2B). Similar experiments carried out with complexes formed between RANTES and heparan sulfate, chondroitin sulfate or dermatan sulfate produced the same results (data not shown), therefore the lack of activity was not specific to heparin binding.

5.6 Analysis of RANTES-Heparin Complex Binding to Cells

Since the soluble RANTES-GAG complexes were unable to elicit an intracellular Ca$^{+2}$ signal, experiments were carried out to determine whether they retained the capacity to bind to cell surfaces. Normal human PBMC were activated, harvested on day 6 of culture, and treated with glycanase cocktail as described in Materials and Methods. FIG. 3, Panel A shows the binding of serial concentrations of $^{125}$I-labeled RANTES complexes (0.03 nM–10 nM of the chemokine component) to treated cells. Panel B, competition binding of 0.3 nM $^{125}$I-labeled RANTES complexes versus serial concentrations of unlabeled RANTES complexes (0.01 nM–100 nM chemokine component). Each data point represents the mean value of triplicate assays. Standard deviation values are shown with bars.

As shown in FIG. 3, experiments performed with $^{125}$I-labeled RANTES—heparin complexes demonstrated dose dependent binding to glycanase treated PBMC that was saturating at 1 nM and higher concentrations (FIG. 3, panel A) and was competitive with respect to non-radioactive RANTES-heparin complexes (FIG. 3, panel B). Flow cytometric analyses of the cells used in these experiments using the anti-CCR5 monoclonal antibody 2D7 (Wu et al. (1997) J Exp Med 186: 1373–81) revealed that 100% of the cells expressed CCR5 (data not shown). Therefore, based on the binding data we calculated a dissociation constant (Kd) of 1.5 nM and a consensus Bmax of approximately 900 binding sites per cell by nonlinear curve fitting after subtracting non-specific binding. This Kd is in good agreement with values reported for the binding of RANTES to 7-TM receptors (Wang et al. (1993) J Exp Medicine 177: 699–705) and suggested that RANTES-GAG complexes retain their ability to bind to cell surface receptors on glycanase treated PBMC.

To further evaluate this possibility, glycanase treated PBMC were incubated with an anti-CCR5 monoclonal antibody (mAb 2D7) known to block RANTES interactions (Wu et al. (1997) J Exp Med 186: 1373–81) and then assayed for binding to soluble $^{125}$I-RANTES-heparin complexes. FIG. 4 is a bar graph showing the inhibition of 125I-labeled RANTES complex binding to glycanase treated PBMC by anti-CCR5 mAb 2D7. Normal human PBMC were activated as previously described and harvested on day 10 of culture to assay binding. Cells were treated with glycanase cocktail for 1 hour. $^{125}$I-RANTES was incubated with heparin (1 mg/ml) for 1 hr at 4° C. $^{125}$I-RANTES complexes were added to cells that had been treated with anti-CCR5 mAb 2D7 (10 μg/ml) (black bar), normal mouse IgG (10 μg/ml) (striped bar), or PBS only (white bar). The values shown reflect average of triplicate assays. Standard deviation values are shown with bars.

As shown in FIG. 4, incubation of cells with mAb 2D7 reduced $^{125}$I-RANTES binding by approximately 40 percent relative to experiments carried out with an isotype control, suggesting that a portion of these complexes interact with cell surface CCR5.

5.7 Inhibition of CCR5-Tropic HIV-1 by RANTES-Heparin Complexes

The ability of the complexes to bind HIV coreceptors was also tested in cell free infectivity assays with PBMC and a primary M-tropic HIV-1 isolate, NSI.03, previously demonstrated to use CCR5 for viral entry (Connor, et al (1997) J Exp Med 185: 621–8). FIG. 5, Panel A is a graph showing the inhibition of HIV-1 replication in PM1 cells by RANTES complexed with GAGs. PBMC were infected with HIV-1 NSI.03 and treated with RANTES, GAG, or RANTES-GAG complexes. RANTES was tested after incubation with heparin (closed triangles), heparan sulfate (closed circles), chondroitin sulfate (open squares) or dermatan sulfate (open circles). Untreated RANTES (closed squares) was tested as a control. The plots reflect the amount of the RANTES component present in each assay. FIG. 5, Panel B is a bar graph showing the results obtained with sham formulations containing only heparin (black bar), heparan sulfate (open bar), chondroitin sulfate (diagonal striped bar) or dermatan sulfate (vertical striped bar) at a concentration matching the highest amount tested in the RANTES-GAG preparations (4 EM). Levels of infection determined 6 days post-infection by HIV-1 p24 antigen capture ELISA are shown. Percent inhibition was determined for each assay relative to the control assays carried out in medium alone. The results obtained with RANTES, heparin and RANTES plus heparin represent the mean of duplicate assays, all other results represent the mean of triplicate assays.

As shown in FIG. 5, Panel A, RANTES-GAG complexes suppressed infection by this isolate in accordance with the cell surface binding data (FIGS. 3 and 4). In contrast, sham formulations containing only GAG at the highest concentration (4 μM, final) used to produce the complexes exhibited lower levels (less than 20%) of virus inhibition (FIG. 5, Panel B) consistent with previous findings (Callahan, et al. (1991) J Virology 65: 1543–50).

FIG. 6 is a bar graph showing the antiviral effects of RANTES-GAG complexes on primary macrophage-tropic HIV isolates which are CCR5 tropic (BaL, NSI.03, and ADA-M) versus HIV-I$_{IIIB}$ which is not CCR5 tropic. Assays were performed using an infectivity reduction format as previously described (Wu et al. (1996) Journal of Virological Methods 69: 2233–39) using activated primary PBMC. The indicated macrophage-tropic isolates BaL, NSI.03, and ADA-M were assayed using a fixed concentration of RANTES (25 nM) in the absence or presence of heparin (250 nM). Control experiments were performed with heparin alone as indicated. Additional control experiments were performed using the T-cell line adapted, SI isolate HIV-I$_{IIIB}$ to verify that the observed virus suppression remained specific for RANTES-CCR5 interactions. These experiments with a panel of primary macrophage-tropic isolates (BaL, NSI.03, and ADA-M) and a fixed concentration of RANTES-GAG complexes (25 nM) revealed variable, yet minor, sensitivities to uncomplexed GAG (FIG. 6). However, in every case the antiviral activity of RANTES was retained after complexing with GAG. In comparison, no inhibition of the T-tropic isolate HIV-IIBB was observed with the RANTES-GAG complexes (FIG. 6) demonstrating that the suppression remained specific for CCR5 tropic viruses.

5.8 Effect of Chemokine-GAG Complexes on Chemotaxis

The promyelocytic cell line HL-60 clone 15 was maintained in RPMI supplemented with 2% PBS and 25 mM N-[2-hydroxyethyl]peperazine-N'-[2-hydroxy-propanesulfonic acid], pH 7.6. The cells were treated with 0.5 MM butyric acid for two days followed by the addition of 10 ng/ml IL-5 to induce the differentiation of these cells to eosinophils (Tiffany, et al. (1998) J. Immunol. 160: 1383–92). Medium was not replenished after the addition of these reagents. Chemotaxis was measured as described in (Martinet, et al. (1994) J Immunol Methods 174:209–14; and Zaitseva et al. (1998) 161: 3103–13) with the following modifications. On day 6 following the addition of butyric acid and IL-5, cells were harvested and resuspended in RPMI 1640 without phenol red or sodium bicarbonate, but with 25 mM Hepes (Life Technologies, Gaithersburg, Md. at a concentation of $1.6 \times 10_6$ cells/ml. Cells were loaded with 0.1 μM Calcein AM (Molecular Probes, Eugene, Oreg.) and an equivalent volume of Pluronic F-127 (Molecular Probes, Eugene, Oreg.) at 37° C. for 30 min. Following the incubation cells were washed twice in the medium described above and resuspendded at a concentration of $4 \times 10^6$ cells/ml. RANTES/GAG complexes were formed as described above. Heparin and RANTES controls were incubated with PBS alone. Dilutions of these reagents were made and were tested in a chemotaxis assay. Chemotaxis was performed in 96-well ChemoTx disposable chambers with 5 µM pores (Neuro Probe, Inc., Gaitheresburg, Md.) (Fevert et al. (1998) J Immunol Methods 213). Chemokines, chemokine/GAG complexes, or PBS alone were placed in the lower chamber in a volume of 29 µl. The filter was then placed on top followed by addition of a 25 µl drop containing $0.1 \times 10^6$ cells. For each experiment, a standard curve was developed to correlate cell number to fluorescence units. The chamber was then placed in a 37° C. incubator for 4 hours. The filter was removed and data were acquired by a Victor (EG&G Wallac, Gaithersburg, Md.). The fluorescence of migrated cells was assessed (Denholm et al. (1995) 19: 366–69) by collecting emission at 517 nM. Each concentration of chemoattractant was tested in duplicate or triplicate.

FIG. 7 shows the effects of the RANTES-heparin chemokine receptor antagonist complex upon chemotaxis in differentiated HL-60 cells. Panel A is the positive control—i.e. the chemotactic response of HL-60 cells to RANTES (3 µM-0.3 nM). Panel C is the negative control—i.e. the response of HL-60 cells to heparin alone (at 30 µM-3 nM). Panel B shows that formation of a RANTES-heparin complex blocks RANTES-induced chemotaxis (30 µM-0.3 nM RANTES component/ 30 µM-3nM Heparin component). Values shown represent the mean of triplicate assays and bars indicate standard deviation.

Taken together, these results clearly demonstrate that soluble complexes formed between β chemokines and GAGs selectively retain antiviral activity yet lack the capacity to activate receptors.

Equivalents

Those skilled in the art will recognize or be able to ascertain using no more than routine experimentation, many equivalents of the specific embodiments of the invention described herein. Such equivalents are intended to be encompassed by the following claims.

What is claimed is:

1. A method of combating HIV-1 virus infection, comprising administering to a patient a pharmaceutically effective amount of a composition which includes:

a chemokine selected from the group consisting of: RANTES, MIP-1α, MIP-1β, MDC, I-309, eotaxin, MCP-3, and SDF-1, and a glycosaminoglycan selected from the group consisting of: heparin, heparin sulfate, chondroitin sulfate, keratan sulfate, and dermatan sulfate.

2. The method of claim 1, wherein the chemokine and the glycosaminoglycan are covalently associated prior to administration to said patient.

3. The method of claim 1, wherein the chemokine and the glycosaminoglycan are noncovalently associated prior to administration to said patient.

4. The method of claim 1, wherein the chemokine is RANTES.

5. The method of claim 1, wherein the chemokine is SDF-1.

6. The method of claim 1, wherein the chemokine is MIP-1α.

7. The method of claim 1, wherein the chemokine is MIP-1β.

8. The method of claim 1, wherein the glycosaminoglycan is heparin.

9. The method of claim 1, wherein the glycosaminoglycan is heparin sulfate.

10. The method of claim 1, wherein the glycosaminoglycan is chondroitin sulfate.

11. The method of claim 1, wherein the glycosaminoglycan is dermatan sulfate.

12. A method of combating HIV-1 virus infection, comprising separately administering to a patient pharmaceutically effective amounts of:

a chemokine selected from the group consisting of: RANTES, MIP-1α, MIP-1β, MDC, I-309, eotaxin, MCP-3, and SDF-1, and a glycosaminoglycan selected from the group consisting of: heparin, heparin sulfate, chondroitin sulfate, keratan sulfate, and dermatan sulfate so that the chemokine and the glycosaminoglycan can combine in vivo and the resulting composition is capable of antagonizing the function of a CXCR4 or a CCR5 chemokine receptor or altering the extracellular recognition of said receptor by HIV-1 virus.

13. The method of claim 12, wherein the chemokine and the glycosaminoglycan are covalently joined.

14. The method of claim 12, wherein the chemokine and the glycosaminoglycan are noncovalently joined.

15. The method of claim 12, wherein said chemokine is RANTES.

16. The method of claim 12, wherein said glycosaminoglycan is heparin.

17. The method of claim 12, wherein said glycosaminoglycan is chondroitin sulfate.

18. The method of claim 12, wherein said chemokine is SDF-1.

19. The method of claim 12, wherein said chemokine is MIP-1α.

20. The method of claim 12, wherein said chemokine is MIP-1β.

21. The method of claim 12, wherein the glycosaminoglycan is dermatan sulfate.

22. The method of claim 12, wherein the glycosaminoglycan is heparin sulfate.

23. A method for inhibiting HIV-1 virus infection, comprising contacting target cells with an effective amount of a composition comprising: a chemokine selected from the group consisting of RANTES, MIP-1α, MIP-1β, MDC, I-309, eotaxin, MCP-3, and SDF-1; and a glycosaminoglycan selected from the group consisting of heparin, heparin sulfate, chondroitin sulfate, keratan sulfate and dermatan sulfate.

24. A method for inhibiting HIV-1 virus infection, comprising contacting target cells with an effective amount of a chemokine selected from the group consisting of RANTES, MIP-1α, MIP-1β, MDC, I-309, eotaxin, MCP-3, and SDF-1; and a glycosaminoglycan selected from the group consisting of heparin, heparin sulfate, chondroitin sulfate, keratan sulfate, and dermatan sulfate, wherein said chemokine and said glycosaminoglycan are complexed or capable of complexing, thereby antagonizing the function of a CXCR4 or a CCR5 chemokine receptor, and altering extracellular recognition of said CXCR4 and said CCR5 receptors by HIV-1 virus.

* * * * *

UNITED STATES PATENT AND TRADEMARK OFFICE
CERTIFICATE OF CORRECTION

PATENT NO. : 6,399,078 B1
DATED : June 4, 2002
INVENTOR(S) : Devico et al.

It is certified that error appears in the above-identified patent and that said Letters Patent is hereby corrected as shown below:

<u>Column 2,</u>
Line 27, "CR3.MAC-1" should be -- CR3, MAC-1 --

<u>Column 3,</u>
Line 34, "extracellular. domains" should be -- extracellular domains --

<u>Column 6,</u>
Line 25, "1-309" should be -- I-309 --

<u>Column 9,</u>
Line 11, "heparan" should be -- heparin --

<u>Column 10,</u>
Line 6, "Campylobacter" should be -- *Campylobacter* --
Line 7, "Enterococcus" should be -- *Enterococcus* --
Line 13, "Leptospira" should be -- *Leptospira* --
Line 22, "is, an" should be -- is an --

<u>Column12,</u>
Line 6, "βchemokine" should be -- β chemokine --
Line 22, "71´:" should be -- 71: --

<u>Column 14,</u>
Line 18, "are. known" should be -- are known --
Line 19, "cells. of" should be -- cells of --

<u>Column 19,</u>
Lines 7 and 22, "Streptococcus" should be -- *Streptococcus* --
Line 11, "Chlamydia" should be -- *Chlamydia* --

<u>Column 21,</u>
Lines 30 and 32, "MIP1β" should be -- MIP-1β --

<u>Column 23,</u>
Line 58, "Klagsbum" should be -- Klagsburn --
Line 64, "selecting" should be -- selectins --

<u>Column 24,</u>
Line 39, "al" should be -- al. --

UNITED STATES PATENT AND TRADEMARK OFFICE
CERTIFICATE OF CORRECTION

PATENT NO.    : 6,399,078 B1
DATED         : June 4, 2002
INVENTOR(S)   : Devico et al.

It is certified that error appears in the above-identified patent and that said Letters Patent is hereby corrected as shown below:

Column 25,
Lines 23 and 29, "oligosaccharides" should be -- oligosaccharide --
Line 33, "example. the" should be -- example, the --

Column 30,
Line 46, "specific-transduction" should be -- specific transduction --

Column 32,
Line 12, "Campylobacter" should be -- *Campylobacter* --
Line 12, "Enterococcus" should be -- *Enterococcus* --
Line 18, "Leptospira" should be -- *Leptospira* --
Line 24, "Bordatella" should be -- *Bordatella* --

Column 33,
Line 51, "B1Atechnology" should be -- BIAtechnology --

Column 34,
Line 6, "micro-centrifuge" should be -- microcentrifuge --

Column 36,
Line 21, "$Ca_{+2}$" should be -- $Ca^{2+}$ --
Line 48, "(1 998)" should be -- (1998) --

Column 37,
Line 65, "94 $\mu$g/ml" should be -- 9 $\mu$g/ml --

Column 38,
Line 9, "a sulfate" should be -- sulfate --
Line 36, "(1 997)" should be -- (1997) --
Line 49, "$Cat^{+2}$" should be -- $Ca^{2+}$ --

Column 39,
Line 28, "125I-labeled" should be -- $^{125}$I-labeled --

UNITED STATES PATENT AND TRADEMARK OFFICE
CERTIFICATE OF CORRECTION

PATENT NO. : 6,399,078 B1
DATED : June 4, 2002
INVENTOR(S) : Devico et al.

It is certified that error appears in the above-identified patent and that said Letters Patent is hereby corrected as shown below:

Column 40,
Line 1, "EM" should be -- $\mu$M --
Line 48, "MM" should be -- $\mu$M --
Line 59, "$1.6 \times 10_6$" should be -- $1.6 \times 10^6$ --

Signed and Sealed this

Twenty-first Day of October, 2003

JAMES E. ROGAN
*Director of the United States Patent and Trademark Office*